(12) United States Patent
Shibasaki et al.

(10) Patent No.: US 9,187,498 B2
(45) Date of Patent: Nov. 17, 2015

(54) COMPOUND AND ASYMMETRIC SYNTHESIS REACTION

(71) Applicant: Microbial Chemistry Research Foundation, Tokyo (JP)

(72) Inventors: Masakatsu Shibasaki, Tokyo (JP); Naoya Kumagai, Tokyo (JP)

(73) Assignee: Microbial Chemistry Research Foundation, Tokyo (JP)

( * ) Notice: Subject to any disclaimer, the term of this patent is extended or adjusted under 35 U.S.C. 154(b) by 0 days.

(21) Appl. No.: 14/658,297

(22) Filed: Mar. 16, 2015

(65) Prior Publication Data

US 2015/0183807 A1 Jul. 2, 2015

Related U.S. Application Data

(60) Division of application No. 14/301,562, filed on Jun. 11, 2014, now Pat. No. 8,981,123, which is a continuation of application No. PCT/JP2012/081042, filed on Nov. 30, 2012.

(30) Foreign Application Priority Data

Dec. 12, 2011 (JP) ................................. 2011-271563

(51) Int. Cl.
| | |
|---|---|
| *C07D 405/12* | (2006.01) |
| *C07D 307/33* | (2006.01) |
| *C07D 215/227* | (2006.01) |
| *C07F 7/08* | (2006.01) |
| *B01J 31/24* | (2006.01) |
| *C07D 309/30* | (2006.01) |
| *C07B 53/00* | (2006.01) |
| *C07C 323/12* | (2006.01) |
| *C07C 381/12* | (2006.01) |
| *C07D 301/02* | (2006.01) |
| *C07D 303/22* | (2006.01) |
| *C07C 323/16* | (2006.01) |
| *C07F 7/12* | (2006.01) |
| *C07F 9/50* | (2006.01) |
| *C07F 9/6561* | (2006.01) |
| *C07F 7/18* | (2006.01) |

(52) U.S. Cl.
CPC ............... *C07F 7/0812* (2013.01); *B01J 31/24* (2013.01); *C07B 53/00* (2013.01); *C07C 323/12* (2013.01); *C07C 323/16* (2013.01); *C07C 381/12* (2013.01); *C07D 215/227* (2013.01); *C07D 301/02* (2013.01); *C07D 303/22* (2013.01); *C07D 307/33* (2013.01); *C07D 309/30* (2013.01); *C07D 405/12* (2013.01); *C07F 7/12* (2013.01); *C07F 7/1844* (2013.01); *C07F 9/5059* (2013.01); *C07F 9/65616* (2013.01)

(58) Field of Classification Search
CPC .. C07F 7/0812; C07D 405/12; C07D 307/33; C07D 215/227
See application file for complete search history.

(56) References Cited

U.S. PATENT DOCUMENTS

| | | |
|---|---|---|
| 5,693,847 A | 12/1997 | Tung et al. |
| 8,183,005 B1 | 5/2012 | Sudo et al. |
| 2006/0194870 A1 | 8/2006 | Sudoh et al. |
| 2006/0217434 A1 | 9/2006 | Aoki et al. |
| 2008/0293950 A1 | 11/2008 | Kato et al. |
| 2011/0098477 A1 | 4/2011 | Aoki et al. |

FOREIGN PATENT DOCUMENTS

| | | |
|---|---|---|
| EP | 2 042 188 | 4/2009 |
| JP | 2002-275127 | 9/2002 |
| JP | 2006-077004 | 3/2006 |
| WO | 2004/071503 | 8/2004 |
| WO | 2005/005372 | 1/2005 |
| WO | 2006/016657 | 2/2006 |
| WO | 2006/088071 | 8/2006 |
| WO | 2007/000994 | 1/2007 |
| WO | 2007/043640 | 4/2007 |
| WO | 2007/132882 | 11/2007 |

OTHER PUBLICATIONS

Sakamoto, H. et al., "Host sphingolipid biosynthesis as a target for hepatitis C virus therapy," Nature Chemical Biology, vol. 1, No. 6, Nov. 2005, pp. 333-337.

Takechi, S., et al., "A Direct Catalytic Asymmetric Aldol Reaction of α-Sulfanyl Lactones: Efficient Synthesis of SPT Inhibitors," Angewandte Chemie International Edition, vol. 51, No. 17, Apr. 23, 2012, pp. 4218-4222.

Takechi, S. et al. "Diastereo Selective Catalytic Asymmetric Direct Aldol Reaction Using α-thiolactone as Nucleophilie," Proceedings of the 132$^{nd}$ Annual Meeting of the Pharmaceutical Society of Japan, vol. 2, Mar. 5, 2012, p. 154, 31E06-pm07S.

Esumi, T. et al., "Synthesis of Viridiofungin A and its Absolute Structure," Proceedings of the 39$^{th}$ Symposium on the Chemistry of Natural Products, Jul. 20, 1997, pp. 409-414, Scheme 2.

Trost, B. et al., "A Synthetic Approach to Polyene Macrolides: Synthesis of the Building Blocks," Tetrahedron Letters, vol. 27, No. 47, 1986, pp. 5691-5694.

(Continued)

*Primary Examiner* — Sun Jae Yoo

(74) *Attorney, Agent, or Firm* — Carmody Torrance Sandak & Hennessey LLP

(57) ABSTRACT

A compound represented by the following General Formula (1):

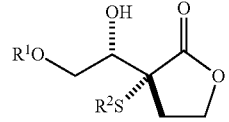

General Formula (1)

where $R^1$ represents a protective group for a hydroxyl group or a hydrogen atom, and $R^2$ represents a methyl group or an ethyl group.

1 Claim, No Drawings

(56) References Cited

OTHER PUBLICATIONS

Tanaka, K. et al., "New Methods for Stereoselective Synthesis of α-Alkylidene-γ-butyrolactones Using Monoanion of O-Ethyl S-(Tetrahydro-2-oxo-3-furanyl) Thiocarbonate and Dianion of α-Mercapto-γ- butyrolactone," Bulletin of the Chemical Society of Japan, vol. 53, No. 10, 1980, pp. 2910-2916.

Yanagisawa, A. et al., "Enantioselective Protonation of Silyl Enalates Catalyzed by a Binap•AgF Complex," Angew. Chem. Int. Ed., vol. 44, 2005, pp. 1546-1548.

Yanagisawa, A. et al., "Enantioselective Addition of Allylic Trimethoxysilanes to Aldehydes Catalyzed by p-Tol-BINAP•AgF," Angew. Chem. Int. Ed., vol. 38, No. 24, 1999, pp. 3701-3703.

Momiyama, N. et al., "Catalyic Enantioselective Synthesis of α-Aminooxy and α-Hydroxy Ketone Using Nitrosobenzene," J. Am. Chem. Soc, vol. 125, 2003, pp. 6038-6039.

Momiyama, N. et al., "Enantioselective O- and N-Nitroso Aldol Synthesis of Tin Enolates. Isolation of Three BINAP-Silver Complexes and Their Role in Regio- and Enantioselectivity," J. Am. Chem. Soc., vol. 126, 2004, pp. 5360-5361.

Yamashita, Y. et al., "Chiral Silver Amide-Catalyzed Enantioselective [3+2] Cycloaddition of α-Aminophosphonates with Olefins," J. Am. Chem. Soc., vol. 132, 2010, pp. 3262-3263.

Yanagisawa, A. et al., "Enantioselective Aldol Reaction of Trimethoxysilyl Enol Ethers with Aldehydes Catalyzed by p-Tol-BINAP•AgF Complex," Synlett 2001, vol. 1, pp. 69-72, ISSN 0936-5214.

Shirakawa, S. et al., "Ag(I)-Catalyzed Michael Additions of β-Ketoesters to Nitroalkenes in Water: Remarkable Effect of Water as a Reaction Medium on Reaction Rates," Synlett 2006, vol. 9, pp. 1410-1412.

COMPOUND AND ASYMMETRIC SYNTHESIS REACTION

CROSS-REFERENCE TO RELATED APPLICATION

This application is a continuation application of International Application PCT/JP2012/081042 filed on Nov. 30, 2012 and designated the U.S., the entire contents of which are incorporated herein by reference.

BACKGROUND OF THE INVENTION

1. Field of the Invention

The present invention relates to a novel compound and an asymmetric synthesis reaction useful for synthesis of a group of compounds including the novel compound.

2. Description of the Related Art

It is said that carriers of hepatitis C virus (HCV) are about two million in Japan and about two hundred million in the world. About 50% of these patients develop chronic hepatitis, and about 20% of them suffer from liver cirrhosis or liver cancer after more than 30 years have passed since infection. Therefore, there has been a demand for establishment of an effective method for treating hepatitis C.

Interferon therapy has been known as an effective method for eliminating HCV. However, patients to which interferon is effective are about ⅓ of all the patients.

In view of this, further developments have been made and at present, a main anti-virus therapy is a PEG-interferon/ribavirin combination therapy using pegylated interferon and ribavirin (1-β-D-ribofuranosyl-1H-1,2,4-triazole-3-carboxyamide) in combination.

However, patients to which even such a PEG-interferon/ribavirin combination therapy is significantly effective are about half of all the patients. Also, the HCV tends to mutate since it is a single-stranded RNA virus, which raises concerns that resistant viruses may arise by use of pharmaceutical drugs targeting viral proteins.

Under such circumstances, demand has arisen for development of an anti-HCV agent targeting host's factors (human cells). The HCV uses the lipid raft portion for anchorage of growth, and hence serine palmitoyltransferase (SPT) inhibitor has been attracting attention, which shows an effect of inhibiting formation of the lipid raft in cells. NA255 expressed by the following structural formula, which is the SPT inhibitor, has been proposed as an anti-HCV agent (see, for example, Sakamoto, H., Okamoto, K. et al., Nat. Chem. Biol., 1,333-337 (2005)).

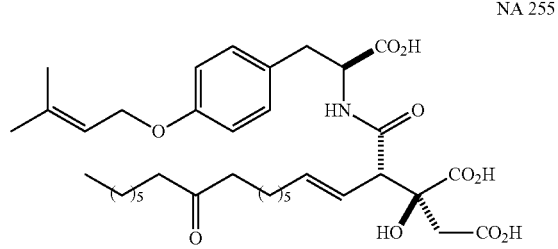

NA 255

The SPT inhibitor involves few side effects and has been expected as an anti-HCV drug.

However, the NA255 is generally produced from *Fusarium* sp. F1476 strain, and cannot be said to be suitable for production on a large scale. Therefore, there has been a demand that such a compound expected as an anti-HCV drug be synthesized by a technique of synthetic organic chemistry.

In one proposal, the NA255 and similar substances are synthesized by a technique of synthetic organic chemistry (see, for example, International Publication No. WO2004/071503). This proposal technique, as shown in the following reaction scheme, synthesizes an optically active substance (compound g) which is an intermediate in syntheses of compounds such as the NA255, and has a problem that it is necessary to use a stoichiometric amount of an asymmetric catalyst (L-(+)-diethyl tartrate/Ti(O$^i$Pr)$_4$).

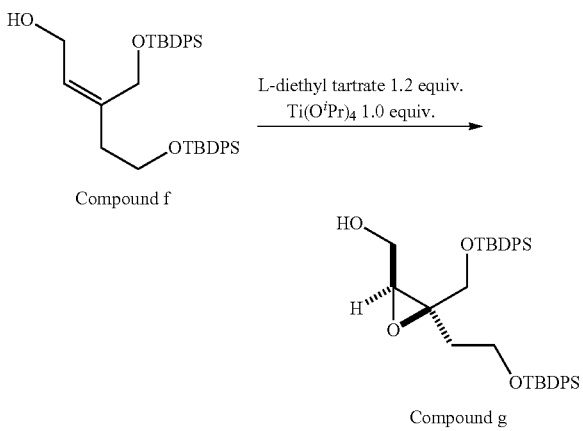

In compound f and compound g, "TBDPS" denotes a tert-butyldiphenylsilyl group, and "O$^i$Pr" denotes an isopropoxy group.

Therefore, at present, there is a demand to provide a novel compound which enables compounds useful for production of pharmaceutical drugs such as anti-hepatitis C virus drugs to be synthesized at low cost by a technique of synthetic organic chemistry; and an asymmetric synthesis reaction useful for synthesis of a group of compounds including the novel compound.

SUMMARY OF THE INVENTION

The present invention aims to solve the above existing and achieve the following object. That is, an object of the present invention is to provide: a novel compound which enables compounds useful for production of pharmaceutical drugs such as anti-hepatitis C virus drugs to be synthesized at low cost by a technique of synthetic organic chemistry; and an asymmetric synthesis reaction useful for synthesis of a group of compounds including the novel compound.

Means for solving the problems are as follows.

<1> A compound represented by the following General Formula (1):

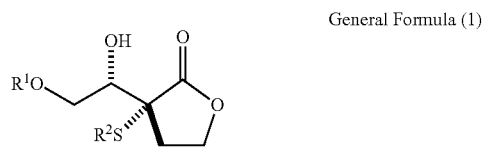

General Formula (1)

where $R^1$ represents a protective group for a hydroxyl group or a hydrogen atom, and $R^2$ represents a methyl group or an ethyl group.

<2> A compound represented by the following General Formula (2):

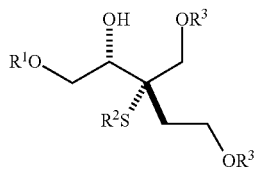

General Formula (2)

where $R^1$ represents a protective group for a hydroxyl group or a hydrogen atom, $R^2$ represents a methyl group or an ethyl group, and $R^3$ represents a protective group for a hydroxyl group or a hydrogen atom.

<3> A compound represented by the following General Formula (3):

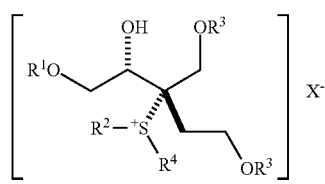

General Formula (3)

where $R^1$ represents a protective group for a hydroxyl group or a hydrogen atom, $R^2$ represents a methyl group or an ethyl group, $R^3$ represents a protective group for a hydroxyl group or a hydrogen atom, $R^4$ represents a methyl group or an ethyl group, and $X^-$ represents a monovalent anion.

<4> An asymmetric synthesis reaction, including:

allowing a compound represented by the following General Formula (4) and a compound represented by the following General Formula (5) to react with each other in the presence of a chiral silver complex obtained from a silver compound and a compound represented by the following General Formula (A) to thereby obtain a compound represented by the following General Formula (6):

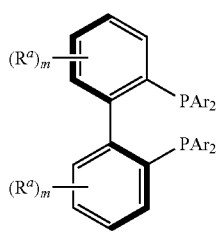

General Formula (A)

where $R^a$ each independently represents a hydrogen atom, an alkyl group, an alkoxy group, an alkenyl group, an aryl group, an arylalkyl group, an arylalkenyl group, a non-aromatic heterocyclic ring, or an aromatic heterocyclic ring, m is an integer of 1 or 2; when m is 2, two $R^a$ may be bonded together to form a ring structure; and Ar represents an aryl group which may have a substituent,

General Formula (4)

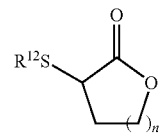

General Formula (5)

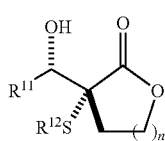

General Formula (6)

where in General Formulas (4) to (6), $R^{11}$ represents a hydrogen atom or a substituent, $R^{12}$ represents a methyl group or an ethyl group, and n is an integer of 1 to 3.

<5> An asymmetric synthesis reaction, including:

allowing a compound represented by the following General Formula (4) and a compound represented by the following General Formula (5) to react with each other in the presence of a chiral silver complex obtained from a silver compound and a compound represented by the following General Formula (B) to thereby obtain a compound represented by the following General Formula (7):

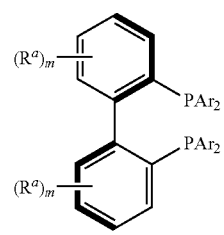

General Formula (B)

where $R^a$ each independently represents a hydrogen atom, an alkyl group, an alkoxy group, an alkenyl group, an aryl group, an arylalkyl group, an arylalkenyl group, a non-aromatic heterocyclic ring, or an aromatic heterocyclic ring, m is an integer of 1 or 2; when m is 2, two $R^a$ may be bonded together to form a ring structure; and Ar represents an aryl group which may have a substituent,

General Formula (4)

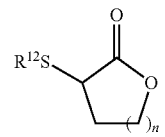

General Formula (5)

-continued

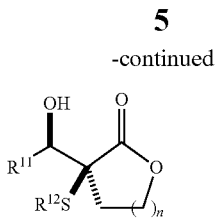

General Formula (7)

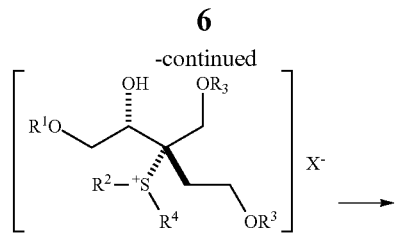

General Formula (3)

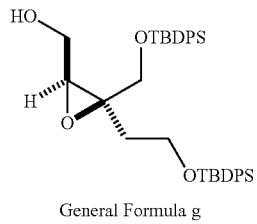

General Formula g where in General Formulas (4) and (7), $R^{11}$ represents a hydrogen atom or a substituent, and in General Formulas (5) and (7), $R^{12}$ represents a methyl group or an ethyl group, and n is an integer of 1 to 3.

The present invention can provide a novel compound which enables compounds useful for production of pharmaceutical drugs such as anti-hepatitis C virus drugs to be synthesized at low cost by a technique of synthetic organic chemistry; and an asymmetric synthesis reaction useful for synthesis of a group of compounds including the novel compound. These can solve the above existing problems and achieve the above object.

DETAILED DESCRIPTION OF THE INVENTION

Unless specifically stated otherwise, steric configuration in chemical formulas and general formulas in the present description and claims is absolute configuration.

(Compound Represented by General Formula (1))

A compound of the present invention is represented by the following General Formula (1).

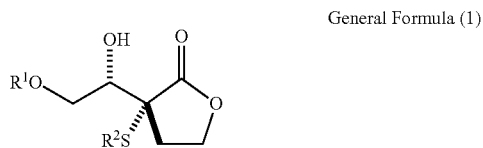

General Formula (1)

where $R^1$ represents a protective group for a hydroxyl group or a hydrogen atom, and $R^2$ represents a methyl group or an ethyl group.

The compound represented by General Formula (1) is a starting material for synthesis of compound g via a compound represented by the following General Formula (2) and a compound represented by the following General Formula (3), as shown in, for example, the following Reaction Scheme (1).

Reaction Scheme (1)

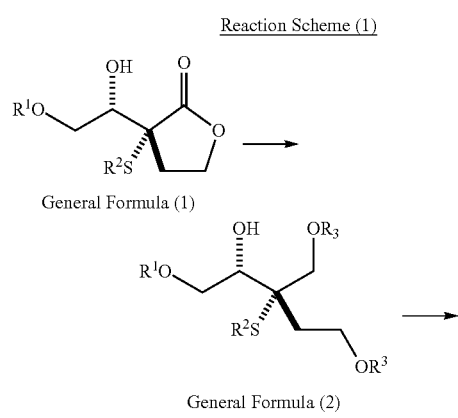

In the compound g, TBDPS denotes a tert-butyldiphenylsilyl group.

In General Formulas (2) and (3), $R^1$ represents a protective group for a hydroxyl group or a hydrogen atom, $R^2$ represents a methyl group or an ethyl group, $R^3$ represents a protective group for a hydroxyl group or a hydrogen atom, $R^4$ represents a methyl group or an ethyl group, and $X^-$ represents a monovalent anion.

As described in International Publication No. WO2004/071503, the compound g is an intermediate in synthesis of a compound useful for anti-hepatitis C virus (HCV) drugs such as a compound represented by General Formula (1') in International Publication No. WO2004/071503 (see Examples of International Publication No. WO2004/071503).

As described above, the compound represented by General Formula (1) is a compound which can be an optically active synthetic element in syntheses of pharmaceutical drugs such as anti-HCV drugs. And, by using the below-described asymmetric synthesis reaction of the present invention found by the present inventors, the compound represented by General Formula (1) can be synthesized using a catalytic amount of a chiral source. Therefore, the compound represented by General Formula (1) can be synthesized at low cost without using a large amount of expensive optically active substances.

The protective group for a hydroxyl group represented by $R^1$ in General Formula (1) is not particularly limited and may be appropriately selected depending on the intended purpose. Reference can be made to documents such as Green et al., Protective Groups in Organic Synthesis, 3rd Edition, 1999, John Wiley & Sons, Inc.

Examples of the protective group for a hydroxyl group include an aralkyl group, a trialkylsilyl group, an alkoxyalkyl group, an alkanoyl group, and an aryl carbonyl group. When the aryl ring in the protective group (e.g., a benzene ring) has a substituent, examples of the substituent include a halogen atom and an alkoxy group.

Examples of the aralkyl group include a benzyl group, a p-methoxybenzyl group (PMB), and a p-aminobenzyl group.

Examples of the trialkylsilyl group include a trimethylsilyl group, a triethylsilyl group, and a tert-butyldimethylsilyl group (TBS).

Examples of the alkoxyalkyl group include a methoxymethyl group and an ethoxymethyl group.

Examples of the alkanoyl group include an acetyl group and a trifluoroacetyl group.

Examples of the aryl carbonyl group include a benzoyl group and a substituted phenyl carbonyl group.

Among these, from the viewpoints of the effects as the protective group and easiness of deprotection reaction in synthesis reaction, an aralkyl group and a trialkylsilyl group are preferable, and a p-methoxybenzyl group (PMB), a benzyl group, and a tert-butyldimethylsilyl group (TBS) are more preferable.

$R^2$ is preferably a methyl group since it is possible to shorten the reaction time of the synthesis of the compound represented by General Formula (1).

A synthesis method of the compound represented by General Formula (1) is not particularly limited and may be appropriately selected depending on the intended purpose. It is preferably synthesis based on the below-described asymmetric synthesis reaction of the present invention.

(Compound Represented by General Formula (2))

A compound of the present invention is represented by the following General Formula (2):

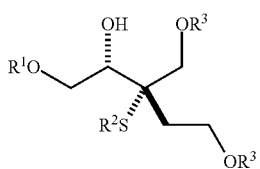

General Formula (2)

where $R^1$ represents a protective group for a hydroxyl group or a hydrogen atom, $R^2$ represents a methyl group or an ethyl group, and $R^3$ represents a protective group for a hydroxyl group or a hydrogen atom.

As shown in the above Reaction Scheme (1), the compound represented by General Formula (2) is useful as an intermediate in the synthesis of the compound g from the compound of the present invention represented by General Formula (1).

The protective group for a hydroxyl group represented by $R^1$ in General Formula (2) is not particularly limited and may be appropriately selected depending on the intended purpose. Examples thereof include the same protective groups as those exemplified for $R^1$ in General Formula (1). Also, preferable protective groups and reasons why they are preferable are the same as in $R^1$ in General Formula (1).

$R^2$ in General Formula (2) is preferably a methyl group since it is possible to shorten the reaction time of the synthesis of a precursor of the compound represented by General Formula (2) (i.e., the compound represented by General Formula (1)).

The protective group for a hydroxyl group represented by $R^3$ in General Formula (2) is not particularly limited and may be appropriately selected depending on the intended purpose. Examples thereof include the same protective groups as those exemplified for $R^1$ in General Formula (1). The protective group for a hydroxyl group is preferably a tert-butyldiphenylsilyl (TBDPS) group from the viewpoint of easiness in the synthesis of the compound g.

A synthesis method of the compound represented by General Formula (2) is not particularly limited and may be appropriately selected depending on the intended purpose. It is, for example, a method of synthesizing the compound represented by General Formula (2) from the compound represented by General Formula (1).

The method of synthesizing the compound represented by General Formula (2) from the compound represented by General Formula (1) is, for example, a method of reducing a lactone to a diol using a reducing agent. The reducing agent is not particularly limited and may be appropriately selected depending on the intended purpose. Examples thereof LiAlH$_4$, NaAlH$_2$ (OC$_2$H$_4$OCH$_3$)$_2$, and NaBH$_4$. A solvent used in this method is not particularly limited and may be appropriately selected depending on the intended purpose. Examples thereof include tetrahydrofuran.

(Compound Represented by General Formula (3))

A compound of the present invention is represented by the following General Formula (3):

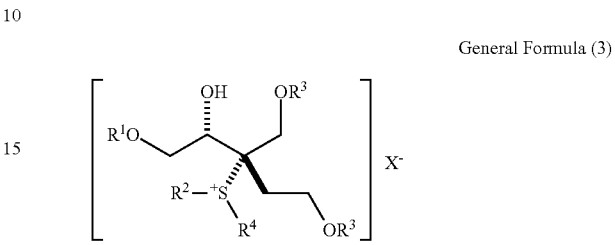

General Formula (3)

where $R^1$ represents a protective group for a hydroxyl group or a hydrogen atom, $R^2$ represents a methyl group or an ethyl group, $R^3$ represents a protective group for a hydroxyl group or a hydrogen atom, $R^4$ represents a methyl group or an ethyl group, and $X^-$ represents a monovalent anion.

As shown in the above Reaction Scheme (1), the compound represented by General Formula (3) is useful as an intermediate in the synthesis of the compound g from the compound of the present invention represented by General Formula (1).

The protective group for a hydroxyl group represented by $R^1$ in General Formula (3) is not particularly limited and may be appropriately selected depending on the intended purpose. Examples thereof include the same protective groups as those exemplified for $R^1$ in General Formula (1). Also, preferable protective groups and reasons why they are preferable are the same as in $R^1$ in General Formula (1).

$R^2$ in General Formula (3) is preferably a methyl group since it is possible to shorten the reaction time of the synthesis of the compound represented by General Formula (1) which is an intermediate in the synthesis of the compound represented by General Formula (3).

The protective group for a hydroxyl group represented by $R^3$ in General Formula (3) is not particularly limited and may be appropriately selected depending on the intended purpose. Examples thereof include the same protective groups as those exemplified for $R^1$ in General Formula (1). The protective group for a hydroxyl group is preferably a tert-butyldiphenylsilyl (TBDPS) group from the viewpoint of easiness in the synthesis of the compound g.

$R^4$ in General Formula (3) is preferably a methyl group since it is possible to perform epoxidation easily to make the synthesis of the compound g easier.

$X^-$ in the General Formula (3) is not particularly limited and may be appropriately selected depending on the intended purpose so long as it is a monovalent anion. Examples thereof include tetrafluoroborate (BF$_4^-$), hexafluorophosphate (PF$_6^-$), and hexafluoroantimonate (SbF$_6^-$). Among these, from the viewpoint of stereoselectivity of asymmetric reaction, hexafluorophosphate (PF$_6^-$) and hexafluoroantimonate (SbF$_6^-$) are preferable.

A synthesis method of the compound represented by General Formula (3) is not particularly limited and may be appropriately selected depending on the intended purpose. It is, for example, a method of synthesizing the compound represented by General Formula (3) from the compound represented by General Formula (2).

The method of synthesizing the compound represented by General Formula (3) from the compound represented by General Formula (2) is, for example, a method of converting a thiomethoxy group or a thioethoxy group to $(R^2R^4)S^+$— using an alkylating agent. The alkylating agent is not particularly limited and may be appropriately selected depending on the intended purpose. Examples thereof include $Me_2Cl$ $(SbF_6)$, $(MeO)_2CHBF_4$, $Me_3OBF_4$, $Et_3OBF_4$, MeOTf, $MeSO_2F$, $(MeO)_2SO_2$, and MeI (where "Me" denotes "methyl group", "Et" denotes "ethyl group", and "Tf" denotes "trifluoromethanesulfonyl group"). A solvent used in this method is not particularly limited and may be appropriately selected depending on the intended purpose. Examples thereof include diethyl ether.

As shown in the above Reaction Scheme (1), the compound represented by General Formula (3) can be a precursor of the compound g, which is a compound useful for anti-hepatitis C virus (HCV) drugs described in International Publication No. WO2004/071503.

(Asymmetric Synthesis Reaction)
<First Asymmetric Synthesis Reaction>

An asymmetric synthesis reaction of the present invention (a first asymmetric synthesis reaction) is allowing a compound represented by the following General Formula (4) and a compound represented by the following General Formula (5) to react with each other in the presence of a chiral silver complex, to thereby obtain a compound represented by the following General Formula (6).

<<Compound Represented by General Formula (4), Compound Represented by General Formula (5), and Compound Represented by General Formula (6)>>

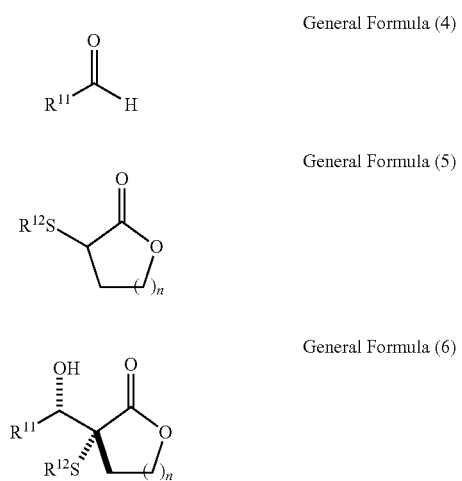

In General Formulas (4) to (6), $R^{11}$ represents a hydrogen atom or a substituent, $R^{12}$ represents a methyl group or an ethyl group, and n is an integer of 1 to 3.

The substituent represented by $R^{11}$ in General Formulas (4) to (6) is not particularly limited and may be appropriately selected depending on the intended purpose. Examples thereof include an alkyl group, an alkenyl group, an aryl group, an arylalkyl group, an arylalkenyl group, a hydroxyalkyl group whose hydroxyl group may be protected, and an aminoalkyl group whose amino group may be protected.

Examples of the alkyl group include an alkyl group having 1 to 20 carbon atoms. Examples of the alkyl group include an isobutyl group and an n-pentyl group.

Examples of the alkenyl group include an alkenyl group having 1 to 20 carbon atoms.

Examples of the aryl group include an aryl group having 1 to 20 carbon atoms.

Examples of the arylalkyl group include an arylalkyl group having 1 to 20 carbon atoms. Examples of the arylalkyl group include a 2-phenylethyl group.

Examples of the arylalkenyl group include an arylalkenyl group having 1 to 20 carbon atoms.

The alkyl group, alkenyl group, aryl group, arylalkyl group, and arylalkenyl group may have, for example, a halogen, a nitro group, and/or a cyano group.

The hydroxyalkyl group whose hydroxyl group may be protected is not particularly limited and may be appropriately selected depending on the intended purpose. Examples of the alkyl group in the hydroxyalkyl group whose hydroxyl group may be protected include an alkyl group having 1 to 20 carbon atoms. The protective group in the hydroxyalkyl group whose hydroxyl group may be protected is not particularly limited and may be appropriately selected depending on the intended purpose so long as it is a protective group for a hydroxyl group. Examples thereof include the same protective groups as those exemplified for $R^1$ in General Formula (1). The hydroxyalkyl group whose hydroxyl group may be protected is preferably a p-methoxybenzyloxymethyl group, a benzyloxymethyl group, or a tert-butyldimethylsilyloxymethyl group.

The aminoalkyl group whose amino group may be protected is not particularly limited and may be appropriately selected depending on the intended purpose. Examples of the alkyl group in the aminoalkyl group whose amino group may be protected include an alkyl group having 1 to 20 carbon atoms. The protective group in the aminoalkyl group whose amino group may be protected is not particularly limited and may be appropriately selected depending on the intended purpose so long as it is a protective group for an amino group. Examples thereof include a methoxycarbonyl group, a tert-butoxycarbonyl group, a benzyloxycarbonyl group, an allyloxycarbonyl group, a formyl group, an acetyl group, a benzoyl group, a methyl group, an ethyl group, an allyl group, a benzenesulfonyl group, and a phthaloyl group.

<<Chiral Silver Complex (First Chiral Silver Complex)>>

The chiral silver complex (first chiral silver complex) is not particularly limited and may be appropriately selected depending on the intended purpose so long as it is a silver complex obtained from a silver compound and a compound represented by the following General Formula (A).

—Silver Compound—

The silver compound is not particularly limited and may be appropriately selected depending on the intended purpose so long as it is a compound capable of forming the chiral silver complex. Examples thereof include $AgPF_6$, $AgBF_4$, $AgSbF_6$, AgOTf (where Tf denotes a trifluoromethylsulfonyl group $(CF_3SO_2^-)$, the same applies hereinafter), $AgClO_4$, $AgNTf_2$, and AgOAc (where Ac denotes an acetyl group). Among these, from the viewpoints of reactivity and stereoselectivity, $AgPF_6$, $AgBF_4$, and $AgSbF_6$ are preferable and $AgPF_6$ is more preferable.

—Compound Represented by General Formula (A)—

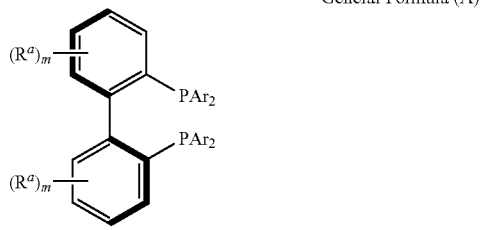

General Formula (A)

where $R^a$ each independently represents a hydrogen atom, an alkyl group, an alkoxy group, an alkenyl group, an aryl group, an arylalkyl group, an arylalkenyl group, a non-aromatic heterocyclic ring, or an aromatic heterocyclic ring, m is an integer of 1 or 2; when m is 2, two $R^a$ may be bonded together to form a ring structure; and Ar represents an aryl group which may have a substituent.

Examples of the alkyl group represented by $R^a$ in General Formula (A) include an alkyl group having 1 to 20 carbon atoms. Examples of the alkyl group having 1 to 20 carbon atoms include a methyl group, an ethyl group, an n-propyl group, an isopropyl group, an n-butyl, an isobutyl, a tert-butyl group, a 1-pentyl group, a 2-pentyl group, a 3-pentyl group, an isopentyl group, a neopentyl group, a tert-pentyl group, a 1-hexyl group, a 2-hexyl group, a 3-hexyl group, a 1-methylethyl-n-pentyl group, a 1,1,2-trimethyl-n-propyl group, a 1,2,2-trimethyl-n-propyl group, a 3,3-dimethyl-n-butyl group, a 1-heptyl group, a 2-heptyl group, 1-ethyl-1,2-dimethyl-n-propyl group, a 1-ethyl-2,2-dimethyl-n-propyl group, a 1-octyl group, a 3-octyl group, a 4-methyl-3-n-heptyl group, a 6-methyl-2-n-heptyl group, a 2-propyl-1-n-heptyl group, a 2,4,4-trimethyl-1-n-pentyl group, a 1-nonyl group, a 2-nonyl group, a 2,6-dimethyl-4-n-heptyl group, a 3-ethyl-2,2-dimethyl-3-n-pentyl group, a 3,5,5-trimethyl-1-n-hexyl group, a 1-decyl group, a 2-decyl group, a 4-decyl group, a 3,7-dimethyl-1-n-octyl group, and a 3,7-dimethyl-3-n-octyl group. Further examples thereof include cyclic alkyl groups such as a cyclopropyl group, a 1-methylcyclopropyl group, a 2-methylcyclopropyl group, a 4-methylcyclohexyl group, a cyclobutyl group, a cyclopentyl group, a cyclohexyl group, a cycloheptyl group, a cyclooctyl group, and a cyclononyl group, cyclodecyl group.

Examples of the alkoxy group represented by $R^a$ in General Formula (A) include an alkoxy group having 1 to 10 carbon atoms. Examples of the alkoxy group having 1 to 10 carbon atoms include a methoxy group, an ethoxy group, an n-propyloxy group, an isopropyloxy group, an n-butyloxy group, a sec-butyloxy group, a tert-butyloxy group, an isobutyloxy group, an n-pentyloxy group, a 2,2-dimethylpropyloxy group, a cyclopentyloxy group, an n-hexyloxy group, a cyclohexyloxy group, a 2-methylpentyloxy group, and a 2-ethylhexyloxy group. Among these, from the viewpoint of stereoselectivity in asymmetric reaction, an alkoxy group having 1 to 5 carbon atoms is preferable, an alkoxy group having 1 to 3 carbon atoms is more preferable, and a methoxy group is particularly preferable.

Examples of the alkenyl group represented by $R^a$ in General Formula (A) include an ethenyl group, a 1-propenyl group, a 2-propenyl group, a 1-butenyl group, a 2-butenyl group, a 3-butenyl group, a 1-pentenyl group, a 2-pentenyl group, a 3-pentenyl group, a 4-pentenyl group, a 1-hexenyl group, a 2-hexenyl group, a 3-hexenyl group, a 4-hexenyl group, and a 5-hexenyl group.

Examples of the aryl group represented by $R^a$ in General Formula (A) include a phenyl group, an α-naphthyl group, a β-naphthyl group, an o-biphenyl group, an m-biphenyl group, a p-biphenyl group, a 1-anthryl group, a 2-anthryl group, a 9-anthryl group, a 1-phenanthryl group, a 2-phenanthryl group, a 3-phenanthryl group, a 4-phenanthryl group, and a 9-phenanthryl group.

Examples of the arylalkyl group represented by $R^a$ in General Formula (A) include a benzyl group, a phenethyl group, a 3-phenylpropyl group, a 4-phenylbutyl group, a 5-phenylpentyl group, a 6-phenylhexyl group, an α-naphthylmethyl group, a β-naphthylmethyl group, an o-biphenylylmethyl group, an m-biphenylylmethyl group, a p-biphenylylmethyl group, a 1-anthrylmethyl group, a 2-anthrylmethyl group, a 9-anthrylmethyl group, a 1-phenanthrylmethyl group, a 2-phenanthrylmethyl group, a 3-phenanthrylmethyl group, a 4-phenanthrylmethyl group, a 9-phenanthrylmethyl group, an α-naphthylethyl group, a β-naphthylethyl group, an o-biphenylylethyl group, an m-biphenylylethyl group, a p-biphenylylethyl group, a 1-anthrylethyl group, a 2-anthrylethyl group, a 9-anthrylethyl group, a 1-phenanthrylethyl group, a 2-phenanthrylethyl group, a 3-phenanthrylethyl group, a 4-phenanthrylethyl group, a 9-phenanthrylethyl group, a biphenylylmethyl group, and a trityl group.

Examples of the arylalkenyl group represented by $R^a$ in General Formula (A) include a 1-phenylethenyl group, a 2-phenylethenyl group, a 1-phenyl-1-propenyl group, a 2-phenyl-1-propenyl group, a 3-phenyl-1-propenyl group, a 1-phenyl-2-propenyl group, a 2-phenyl-2-propenyl group, a 3-phenyl-2-propenyl group, a 1-phenyl-1-butenyl group, a 2-phenyl-1-butenyl group, a 3-phenyl-1-butenyl group, a 4-phenyl-1-butenyl group, a 1-phenyl-2-butenyl group, a 2-phenyl-2-butenyl group, a 3-phenyl-2-butenyl group, a 4-phenyl-2-butenyl group, a 1-phenyl-3-butenyl group, a 2-phenyl-3-butenyl group, a 3-phenyl-3-butenyl group, a 4-phenyl-3-butenyl group, a 5-phenyl-1-pentenyl group, a 5-phenyl-2-pentenyl group, a 5-phenyl-3-pentenyl group, a 5-phenyl-4-pentenyl group, a 6-phenyl-1-hexenyl group, a 6-phenyl-2-hexenyl group, a 6-phenyl-3-hexenyl group, a 6-phenyl-4-hexenyl group, and a 6-phenyl-5-hexenyl group.

Examples of the non-aromatic heterocyclic ring represented by $R^a$ in General Formula (A) include a 5-membered to 7-membered monoheterocyclic ring group and a fused diheterocyclic ring group having 6 to 10 constituent atoms. These may contain 1 to 3 oxygen atoms, 1 to 3 nitrogen atoms, 1 to 3 sulfur atoms, or 1 to 3 atoms of any combination thereof. Examples of the non-aromatic heterocyclic ring include a 2-tetrahydrofuranyl group, a 3-tetrahydrofuranyl group, a 2-tetrahydropyranyl group, a 3-tetrahydropyranyl group, a 4-tetrahydropyranyl group, a 1-pyrrolidinyl group, a 2-pyrrolidinyl group, a 3-pyrrolidinyl group, a 1-pyrrolinyl group, a 2-pyrrolinyl group, a 3-pyrrolinyl group, a 4-pyrrolinyl group, a 5-pyrrolinyl group, a 1-imidazolidinyl group, a 2-imidazolidinyl group, a 4-imidazolidinyl group, a 1-imidazolinyl group, a 2-imidazolinyl group, a 4-imidazolinyl group, a 1-pyrazolidinyl group, a 3-pyrazolidinyl group, a 4-pyrazolidinyl group, a 1-pyrazolinyl group, a 2-pyrazolinyl group, a 3-pyrazolinyl group, a 4-pyrazolinyl group, a 5-pyrazolinyl group, a 1-piperidyl group, a 2-piperidyl group, a 3-piperidyl group, a 4-piperidyl group, a 1-piperazinyl group, a 2-piperazinyl group, a 3-piperazinyl group, a 1-indolinyl group, a 2-indolinyl group, a 3-indolinyl group, a 4-indolinyl group, a 5-indolinyl group, a 6-indolinyl group, a 7-indolinyl group, a 1-isoindolinyl group, a 2-isoindolinyl group, a 4-isoindolinyl group, a 5-isoindolinyl group, a 2-quinuclidinyl group, a 3-quinuclidinyl group, a 4-quinuclidinyl group, a 2-morpholinyl group, a 3-morpholinyl group, a 4-morpholinyl group, a 1-azetidinyl group, a 2-azetidinyl group, a 3-azetidinyl group, a 1-azetidinonyl group, a 3-azetidinonyl group, and a 4-azetidinonyl group.

Examples of the aromatic heterocyclic ring represented by $R^a$ in General Formula (A) include a 5-membered to 7-membered monocyclic ring group and a fused di-heterocyclic ring group having 8 to 10 constituent atoms. These may contain 1 to 3 oxygen atoms, 1 to 3 nitrogen atoms, 1 to 3 sulfur atoms, or 1 to 3 atoms of any combination thereof. Examples of the aromatic heterocyclic ring include a 2-thienyl group, a 3-thienyl group, a 2-furyl group, a 3-furyl group, a 2-pyranyl group, a 3-pyranyl group, a 4-pyranyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 4-isobenzofuranyl group, a 5-isobenzofuranyl group, a 2-benzothienyl group, a 3-benzothienyl group, a 4-benzothienyl group, a 5-benzothienyl group, a 6-benzothienyl group, a 7-benzothienyl group, a 1-isobenzothienyl group, a 4-isobenzothienyl group, a 5-isobenzothienyl group, a 2-chromenyl group, a 3-chromenyl group, a 4-chromenyl group, a 5-chromenyl group, a 6-chromenyl group, a 7-chromenyl group, a 8-chromenyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 2-oxazolyl group, a 4-oxazolyl group, a 5-oxazolyl group, a 3-isooxazolyl group, a 4-isooxazolyl group, a 5-isooxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group, a 4-pyridazinyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 1-isoindolyl group, a 4-isoindolyl group, a 5-isoindolyl group, a 1-indolyl group, a 2-indolyl group, a 3-indolyl group, a 4-indolyl group, a 5-indolyl group, a 6-indolyl group, a 7-indolyl group, a 1-indazolyl group, a 2-indazolyl group, a 3-indazolyl group, a 4-indazolyl group, a 5-indazolyl group, a 6-indazolyl group, a 7-indazolyl group, a 1-purinyl group, a 2-purinyl group, a 3-purinyl group, a 6-purinyl group, a 7-purinyl group, a 8-purinyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 1-phthalazinyl group, a 5-phthalazinyl group, a 6-phthalazinyl group, a 2-naphthyridinyl group, a 3-naphthyridinyl group, a 4-naphthyridinyl group, a 2-quinoxalinyl group, a 5-quinoxalinyl group, a 6-quinoxalinyl group, a 2-quinazolinyl group, a 4-quinazolinyl group, a 5-quinazolinyl group, a 6-quinazolinyl group, a 7-quinazolinyl group, a 8-quinazolinyl group, a 3-cinnolinyl group, a 4-cinnolinyl group, a 5-cinnolinyl group, a 6-cinnolinyl group, a 7-cinnolinyl group, a 8-cinnolinyl group, a 2-pteridinyl group, a 4-pteridinyl group, a 6-pteridinyl group, a 7-pteridinyl group, and a 3-furazanyl group.

The compound represented by General Formula (A) and having a ring structure in which two $R^a$ are bonded together when m is 2 is not particularly limited and may be appropriately selected depending on the intended purpose. Examples thereof include a compound represented by General Formula (A) having a bipiperonyl skeleton. Specific examples thereof include a compound represented by the following General Formula (A-2).

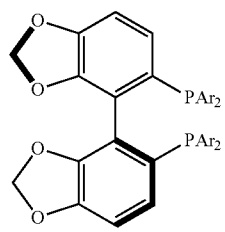

General Formula (A-2)

In General Formula (A-2), Ar denotes a 3,5-di-tert-butyl-4-methoxyphenyl group.

Ar in General Formula (A) is not particularly limited and may be appropriately selected depending on the intended purpose so long as it is an aryl group which may have a substituent.

The aryl group is not particularly limited and may be appropriately selected depending on the intended purpose. Examples thereof include the aryl groups exemplified for the explanation of $R^a$. Among these, a phenyl group is preferable.

The substituent in the aryl group which may have a substituent is not particularly limited and may be appropriately selected depending on the intended purpose. Examples thereof include an alkyl group and an alkoxy group.

The alkyl group is preferably an alkyl group having 1 to 10 carbon atoms, more preferably an alkyl group having 1 to 6 carbon atoms, particularly preferably an alkyl group having 1 to 4 carbon atoms. Examples thereof include a methyl group, an ethyl group, an n-propyl group, an isopropyl group, an n-butyl group, an isobutyl group, and a tert-butyl group. Among these, a tert-butyl group is preferable.

The alkoxy group is preferably an alkoxy group having 1 to 10 carbon atoms, more preferably an alkoxy group having 1 to 6 carbon atoms, particularly preferably an alkoxy group having 1 to 4 carbon atoms. Examples of the alkoxy group having 1 to 4 carbon atoms include a methoxy group, an ethoxy group, an n-propyl group, an isopropyl group, an n-butyloxy group, a sec-butoxy group, a tert-butoxy group, and an isobutyl group. Among these, a methoxy group is preferable.

The substitution position of the substituent in the aryl group which may have a substituent is not particularly limited and may be appropriately selected depending on the intended purpose.

The number of the substituents on the aryl group is not particularly limited and may be appropriately selected depending on the intended purpose. It is, for example, 1 to 3.

From the viewpoint of stereoselectivity in asymmetric reaction, the compound represented by General Formula (A) is a compound represented by the following General Formula (A-1).

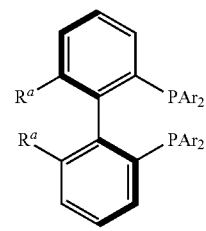

Chemical Formula (A-1)

In General Formula (A-1), $R^a$ represents a methoxy group, and Ar represents a 3,5-di-tert-butyl-4-methoxyphenyl group.

—Synthesis Method of Chiral Silver Complex (First Chiral Silver Complex)—

A synthesis method of the chiral silver complex (first chiral silver complex) is not particularly limited and may be appropriately selected depending on the intended purpose. In one exemplary method, the chiral silver complex is obtained by mixing the silver compound and the compound represented by General Formula (A) in an inert atmosphere, optionally in a solvent.

The amounts of the silver compound and the compound represented by General Formula (A) used in the synthesis of the chiral silver complex (first chiral silver complex) are not particularly limited and may be appropriately selected depending on the intended purpose. The amount of the compound represented by General Formula (A) is preferably 1.0 mol to 2.0 mol, more preferably 1.0 mol to 1.1 mol, relative to 1.0 mol of the silver compound. When the compound represented by General Formula (A) is less than 1.0 mol, its stereoselectivity may decrease, whereas when it is more than 2.0 mol, its catalytic activity may decrease. The amount of the compound represented by General Formula (A) falling within the above more preferable range is advantageous in terms of stereoselectivity and catalytic activity.

The inert atmosphere is not particularly limited and may be appropriately selected depending on the intended purpose. It is, for example, an argon atmosphere.

The solvent is not particularly limited and may be appropriately selected depending on the intended purpose. It is, for example, toluene. The toluene is preferably anhydrous toluene.

The reaction temperature in the synthesis of the chiral silver complex is not particularly limited and may be appropriately selected depending on the intended purpose. It is, for example, room temperature. The room temperature is, for example, 20° C. to 30° C.

The reaction time in the synthesis of the chiral silver complex is not particularly limited and may be appropriately selected depending on the intended purpose. It is, for example, 0.5 hours to 1 hour.

<<Reaction Conditions for Asymmetric Synthesis Reaction (First Asymmetric Synthesis Reaction)>>

In the asymmetric synthesis reaction (first asymmetric synthesis reaction), a compound represented by General Formula (6) can be obtained by allowing the compound represented by General Formula (4) and the compound represented by General Formula (5) to react with each other using the chiral silver complex and optionally a catalytic amount of a base.

—Base—

The base is not particularly limited and may be appropriately selected depending on the intended purpose. Examples thereof include diazabicycloundecene (DBU, 1,8-diazabicyclo[5.4.0]undec-7-ene), triethylamine, 1,5,7-triazabicyclo[4.4.0]dec-5-ene, and N, N-diisopropylethylamine.

An amount of the base used is not particularly limited and may be appropriately selected depending on the intended purpose. It is preferably 0.5 mol % to 10 mol %, more preferably 1 mol % to 8 mol %, particularly preferably 2 mol % to 6 mol %, relative to the compound represented by General Formula (5). When the amount of the base used is less than 0.5 mol %, reaction may not proceed successfully, whereas when it is more than 10 mol %, side reactions may proceed. The amount of the base falling within the above particularly preferable range is advantageous in terms of stereoselectivity and catalytic activity.

Also, the amount of the base used is preferably 0.8 mol to 2 mol relative to 1 mol of an amount of the chiral silver complex used, described below.

—Amount of Chiral Silver Complex Used—

An amount of the chiral silver complex used in the asymmetric synthesis reaction (first asymmetric synthesis reaction) is not particularly limited and may be appropriately selected depending on the intended purpose. It is preferably 0.5 mol % to 10 mol %, more preferably 1 mol % to 8 mol %, particularly preferably 2 mol % to 6 mol %, relative to the compound represented by General Formula (5). When the amount of the chiral silver complex used is less than 0.5 mol %, stereoselectivity may decrease, whereas when it is more than 10 mol %, the amount of the catalyst is large, potentially leading to higher cost for the synthesis. The amount of the chiral silver complex falling within the above particularly preferable range is advantageous since high stereoselectivity can be obtained and asymmetric synthesis reaction can be performed at low cost.

—Amount of the Compound Represented by General Formula (4) Used—

An amount of the compound represented by General Formula (4) used in the asymmetric synthesis reaction (first asymmetric synthesis reaction) is not particularly limited and may be appropriately selected depending on the intended purpose. It is preferably 1 mol or more, more preferably 1 mol to 2 mol, particularly preferably 1.1 mol to 1.5 mol, relative to 1 mol of the compound represented by General Formula (5). When the amount of the compound represented by General Formula (4) is less than 1 mol, reaction yield may decrease, whereas when it is more than 2 mol, much time and effort may be needed for purification. The amount of the compound represented by General Formula (4) falling within the above particularly preferable range is advantageous since reaction yield is good and synthesis can be performed without much time and effort for purification.

—Organic Solvent—

An organic solvent is preferably used in the asymmetric synthesis reaction (first asymmetric synthesis reaction). The organic solvent is not particularly limited and may be appropriately selected depending on the intended purpose. Examples thereof include toluene, tetrahydrofuran (THF), and methylene chloride. An amount of the organic solvent used is not particularly limited and may be appropriately selected depending on the intended purpose.

—Reaction Temperature—

The reaction temperature in the asymmetric synthesis reaction (first asymmetric synthesis reaction) is not particularly limited and may be appropriately selected depending on the intended purpose. It is preferably −40° C. to 20° C., more preferably −30° C. to 10*C, particularly preferably −25° C. to −15° C. When the reaction temperature is lower than −40° C., the progress of reaction may be slow, whereas when it is higher than 20° C., stereoselectivity may decrease. The reaction temperature falling within the above particularly preferable range is advantageous in terms of stereoselectivity and catalytic activity.

—Reaction Time—

The reaction time of the asymmetric synthesis reaction (first asymmetric synthesis reaction) is not particularly limited and may be appropriately selected depending on the intended purpose. It is preferably 6 hours to 72 hours, more preferably 12 hours to 36 hours, particularly preferably 20 hours to 28 hours. When the reaction time is less than 6 hours, reaction yield may decrease, whereas when it is more than 72 hours, side reactions may proceed. The reaction time falling within the above particularly preferable range is advantageous in terms of reaction yield.

<Second Asymmetric Synthesis Reaction>

An asymmetric synthesis reaction of the present invention (second asymmetric synthesis reaction) includes allowing a compound represented by the following General Formula (4) and a compound represented by the following General Formula (5) to react with each other in the presence of a chiral silver complex, to thereby obtain a compound represented by the following General Formula (7).

<<Compound Represented by General Formula (4), Compound Represented by General Formula (5), and Compound Represented by General Formula (7)>>

General Formula (4)

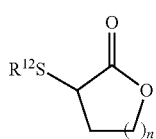

General Formula (5)

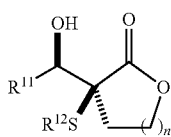

General Formula (7)

In General Formulas (4) and (7), $R^{11}$ represents a hydrogen atom or a substituent, and in General Formulas (5) and (7), $R^{12}$ represents a methyl group or an ethyl group, and n is an integer of 1 to 3.

Examples of the substituent represented by $R^{11}$ in General Formulas (4) and (7) include the same substituents as those exemplified for the explanation of $R^{11}$ in General Formulas (4) to (6) in the first asymmetric synthesis reaction. Preferable examples are also the same.

<<Chiral Silver Complex (Second Chiral Silver Complex)>>

The chiral silver complex (second chiral silver complex) is not particularly limited and may be appropriately selected depending on the intended purpose so long as it is a silver complex obtained from a silver compound and a compound represented by the following General Formula (B).

—Silver Compound—

The silver compound is not particularly limited and may be appropriately selected depending on the intended purpose so long as it is a compound capable of forming the chiral silver complex. Examples thereof include $AgPF_6$, $AgBF_4$, $AgSbF_6$, AgOTf (where Tf denotes a trifluoromethylsulfonyl group $(CF_3SO_2^-)$, the same applies hereinafter), $AgClO_4$, $AgNTf_2$, and AgOAc (where Ac denotes an acetyl group). Among these, from the viewpoints of reactivity and stereoselectivity, $AgPF_6$, $AgBF_4$, and $AgSbF_6$ are preferable and $AgPF_6$ is more preferable.

—Compound Represented by General Formula (B)—

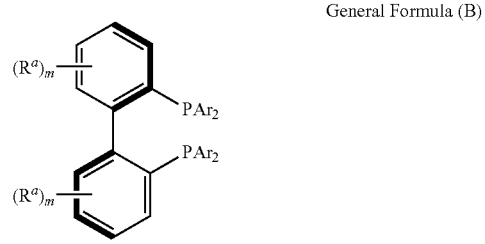

General Formula (B)

where $R^a$ each independently represents a hydrogen atom, an alkyl group, an alkoxy group, an alkenyl group, an aryl group, an arylalkyl group, an arylalkenyl group, a non-aromatic heterocyclic ring, or an aromatic heterocyclic ring, m is an integer of 1 or 2; when m is 2, two $R^a$ may be bonded together to form a ring structure; and Ar represents an aryl group which may have a substituent.

Examples of the alkyl group, alkoxy group, alkenyl group, aryl group, arylalkyl group, arylalkenyl group, non-aromatic heterocyclic ring, or aromatic heterocyclic ring represented by $R^a$ in General Formula (B) include the same groups as the alkyl group, alkoxy group, alkenyl group, aryl group, arylalkyl group, arylalkenyl group, non-aromatic heterocyclic ring, or aromatic heterocyclic ring exemplified for $R^a$ in General Formula (A). Preferable examples are also the same.

The compound represented by General Formula (B) and having a ring structure in which two $R^a$ are bonded together when m is 2 is not particularly limited and may be appropriately selected depending on the intended purpose. Examples thereof include a compound represented by General Formula (B) having a bipiperonyl skeleton.

Examples of Ar in General Formula (B) include the same groups as those exemplified for Ar in General Formula (A) in the explanation of the first asymmetric synthesis reaction. Preferable examples are also the same.

The compound represented by General Formula (B) is preferably a compound represented by the following General Formula (B-1) from the viewpoint of stereoselectivity in asymmetric reaction.

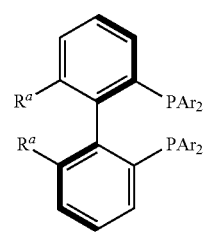

General Formula (B-1)

In General Formula (B-1), $R^a$ represents a methoxy group, and Ar denotes a 3,5-di-tert-butyl-4-methoxyphenyl group.

—Synthesis Method of Chiral Silver Complex—

A synthesis method of the chiral silver complex (second chiral silver complex) is not particularly limited and may be appropriately selected depending on the intended purpose. In one exemplary method, the chiral silver complex is obtained by mixing the silver compound and the compound represented by General Formula (B) in an inert atmosphere, optionally in a solvent.

Preferable ranges of the silver compound and the compound represented by General Formula (B) used in the synthesis of the chiral silver complex (second chiral silver complex) are the same as the amounts of the silver compound and the compound represented by General Formula (A) used in the synthesis of the chiral silver complex (first chiral silver complex). Reasons why the preferable rages are preferable are also the same.

The inert atmosphere, solvent, reaction temperature, and reaction time in the synthesis of the chiral silver complex (second chiral silver complex) are, for example, the same inert atmosphere, solvent, reaction temperature, and reaction time in the synthesis of the chiral silver complex (first chiral silver complex). Preferable examples are also the same.

<<Reaction Conditions for Asymmetric Synthesis Reaction (Second Asymmetric Synthesis Reaction)>>

In the asymmetric synthesis reaction (second asymmetric synthesis reaction), a compound represented by General Formula (7) can be obtained by allowing the compound represented by General Formula (4) and the compound represented by General Formula (5) to react with each other using the chiral silver complex and optionally a catalytic amount of a base.

—Base—

The base is not particularly limited and may be appropriately selected depending on the intended purpose. Examples thereof include diazabicycloundecene (DBU, 1,8-diazabicyclo[5.4.0]undec-7-ene), triethylamine, 1,5,7-triazabicyclo[4.4.0]dec-5-ene, and N, N-diisopropylethylamine.

A preferable range of an amount of the base used is the same as the preferable range of the amount of the base used in the asymmetric synthesis reaction (first asymmetric synthesis reaction). Reasons why the preferable rage is preferable are also the same.

—Amount of Chiral Silver Complex Used—

An amount of the chiral silver complex used in the asymmetric synthesis reaction (second asymmetric synthesis reaction) is not particularly limited and may be appropriately selected depending on the intended purpose. It is preferably 0.5 mol % to 10 mol %, more preferably 1 mol % to 8 mol %, particularly preferably 2 mol % to 6 mol %, relative to the compound represented by General Formula (5). When the amount of the chiral silver complex used is less than 0.5 mol %, stereoselectivity may decrease, whereas when it is more than 10 mol %, the amount of the catalyst is large, potentially leading to higher cost for the synthesis. The amount of the chiral silver complex falling within the above particularly preferable range is advantageous since high stereoselectivity can be obtained and asymmetric synthesis reaction can be performed at low cost.

—Amount of the Compound Represented by General Formula (4) Used—

An amount of the compound represented by General Formula (4) used in the asymmetric synthesis reaction (second asymmetric synthesis reaction) is not particularly limited and may be appropriately selected depending on the intended purpose. It is preferably 1 mol or more, more preferably 1 mol to 2 mol, particularly preferably 1.1 mol to 1.5 mol, relative to 1 mol of the compound represented by General Formula (5). When the amount of the compound represented by General Formula (4) is less than 1 mol, reaction yield may decrease, whereas when it is more than 2 mol, much time and effort may be needed for purification. The amount of the compound represented by General Formula (4) falling within the above particularly preferable range is advantageous since reaction yield is good and synthesis can be performed without much time and effort for purification.

—Organic Solvent—

An organic solvent is preferably used in the asymmetric synthesis reaction (second asymmetric synthesis reaction). The organic solvent is not particularly limited and may be appropriately selected depending on the intended purpose. Examples thereof include toluene, tetrahydrofuran (THF), and methylene chloride. An amount of the organic solvent used is not particularly limited and may be appropriately selected depending on the intended purpose.

Preferable ranges of the reaction temperature and the reaction time in the asymmetric synthesis reaction (second asymmetric synthesis reaction) are the same as the preferable ranges of the reaction temperature and the reaction time in the asymmetric synthesis reaction (first asymmetric synthesis reaction). Reasons why the preferable rage is preferable are also the same.

The compound of the present invention represented by General Formula (1) can be synthesized by the above-described asymmetric synthesis reaction of the present invention without using an expensive asymmetric catalyst in a large amount. As shown in Reaction Scheme (1), the compound represented by General Formula (1) can also be used for the synthesis of the compound g which is an intermediate in synthesis of a compound useful for anti-hepatitis C virus drugs described in International Publication No. WO2004/071503. In addition, a so-called serine palmitoyltransferase (SPT) inhibitor described in International Publication No. WO2004/071503 is expected to be effective to other diseases than hepatitis C. Therefore, the compound represented by General Formula (1) enables compounds useful for production of pharmaceutical drugs such as anti-hepatitis C virus drugs to be synthesized at low cost by a technique of synthetic organic chemistry.

The compound of the present invention represented by General Formula (2) can be synthesized from the compound represented by General Formula (1). As shown in Reaction Scheme (1), the compound represented by General Formula (2) can also be used for the synthesis of the compound g which is an intermediate in synthesis of a compound useful for anti-hepatitis C virus drugs described in International Publication No. WO2004/071503. In addition, a so-called SPT inhibitor described in International Publication No. WO2004/071503 is expected to be effective to other diseases than hepatitis C. Therefore, the compound represented by General Formula (2) enables compounds useful for production of pharmaceutical drugs such as anti-hepatitis C virus drugs to be synthesized at low cost by a technique of synthetic organic chemistry.

The compound of the present invention represented by General Formula (3) can be synthesized from the compound represented by General Formula (2). As shown in Reaction Scheme (1), the compound represented by General Formula (3) can also be used for the synthesis of the compound g which is an intermediate in synthesis of a compound useful for anti-hepatitis C virus (HCV) drugs described in International Publication No. WO2004/071503. In addition, a so-called SPT inhibitor described in International Publication No. WO2004/071503 is expected to be effective to other diseases than hepatitis C. Therefore, the compound represented by General Formula (3) enables compounds useful for production of pharmaceutical drugs such as anti-hepatitis C virus drugs to be synthesized at low cost by a technique of synthetic organic chemistry.

As described above, the asymmetric synthesis reaction of the present invention enables compounds useful for production of pharmaceutical drugs such as anti-hepatitis C virus drugs to be synthesized at low cost by a technique of synthetic organic chemistry.

EXAMPLES

The present invention will next be described in detail by way of Examples. The present invention should not be construed as being limited to the Examples.

In the following Examples, "Me" denotes a "methyl group". "THF" denotes "tetrahydrofuran". "DMF" denotes "N,N-dimethylformamide". "Bn" denotes a "benzyl group". "PMB" denotes a "p-methoxybenzyl group". "TBDPS" denotes a "tert-butyldiphenylsilyl group". "TBS" denotes a "tert-butyldimethylsilyl group". "Ph" denotes a "phenyl group". "rt" denotes room temperature.

Production Example 1

<Preparation of catalyst (chiral silver complex) solution 1>

In a glove box, $AgPF_6$ (22.8 mg, 0.09 mmol) and (S)-3,5-di-tert-butyl-4-methoxy-methoxy BIPHEP (min. 97%) ((S)-3,5-di-$^t$Bu-4-MeO-MeOBIPHEP, the following General Formula (A-1), 106.8 mg, 0.09 mmol) were weighed in a 50 mL-blown recovery flask which had been dried under heating and vacuum. The flask was taken out from the glove box, and anhydrous toluene (14.8 mL) was added thereto in an argon atmosphere, followed by stirring at room temperature for 30 min, to thereby obtain catalyst solution 1.

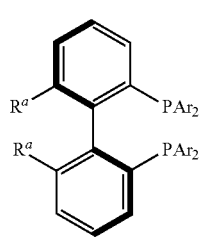

General Formula (A-1)

In General Formula (A-1), $R^a$ represents a methoxy group, and Ar represents a 3,5-di-tert-butyl-4-methoxyphenyl group.

Production Example 2

<Preparation of Catalyst (Chiral Silver Complex) Solution 2>

In a glove box, $AgSbF_6$ (97%, 3.5 mg, 0.01 mmol, 0.05 equivalents) and (S)-3,5-di-$^t$Bu-4-MeO-MeOBIPHEP (min. 97%, 11.9 mg, 0.01 mmol, 0.05 equivalents, the above General Formula (A-1)) were weighed in a brown test tube which had been dried under heating and vacuum. The test tube was taken out from the glove box, and anhydrous toluene (0.98 mL) was added thereto in an argon atmosphere, followed by stirring at room temperature for 30 min, to thereby obtain catalyst solution 2.

Production Example 3

<Preparation of Catalyst (Chiral Silver Complex) Solution 3>

In a glove box, $AgBF_4$ (98%, 2.0 mg, 0.01 mmol, 0.05 equivalents) and (S)-3,5-di-$^t$Bu-4-MeO-MeOBIPHEP (min. 97%, 11.9 mg, 0.01 mmol, 0.05 equivalents, the General Formula (A-1)) were weighed in a brown test tube which had been dried under heating and vacuum. The test tube was taken out from the glove box, and anhydrous toluene (0.98 mL) was added thereto in an argon atmosphere, followed by stirring at room temperature for 30 min, to thereby obtain catalyst solution 3.

Production Example 4

<Preparation of Catalyst (Chiral Silver Complex) Solution 4>

In a glove box, $AgPF_6$ (2.5 mg, 0.01 mmol, 0.05 equivalents) and (S)-DTBM-SEGPHOS (11.8 mg, 0.01 mmol, 0.05 equivalents, the following General Formula (A-2)) were weighed in a brown test tube which had been dried under heating and vacuum. The test tube was taken out from the glove box, and anhydrous toluene (0.98 mL) was added thereto in an argon atmosphere, followed by stirring at room temperature for 30 min, to thereby obtain catalyst solution 4.

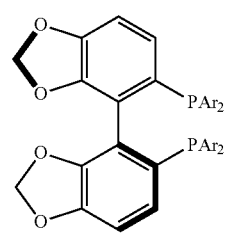

General Formula (A-2)

In General Formula (A-2), Ar denotes a 3,5-di-tert-butyl-4-methoxyphenyl group.

Production Example 5

<Preparation of Catalyst (Chiral Silver Complex) Solution 5>

In a glove box, $AgPF_6$ (10.1 mg, 0.04 mmol) and (R)-3,5-di-$^t$Bu-4-MeO-MeOBIPHEP (min. 97%, 47.5 mg, 0.04 mmol, the following General Formula (B-1)) were weighed in a brown test tube which had been dried under heating and vacuum. The test tube was taken out from the glove box, and anhydrous toluene (0.8 mL) was added thereto in an argon atmosphere, followed by stirring at room temperature for 30 min, to thereby obtain catalyst solution 5 (0.05 M toluene solution).

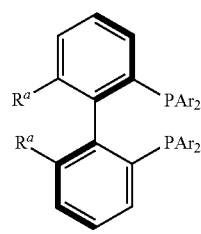

General Formula (B-1)

In General Formula (B-1), $R^a$ represents a methoxy group, and Ar denotes a 3,5-di-tert-butyl-4-methoxyphenyl group.

First, the overall scheme of the Examples 1-1 to 1-5 will be given below.

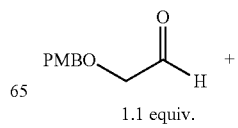

1.1 equiv.

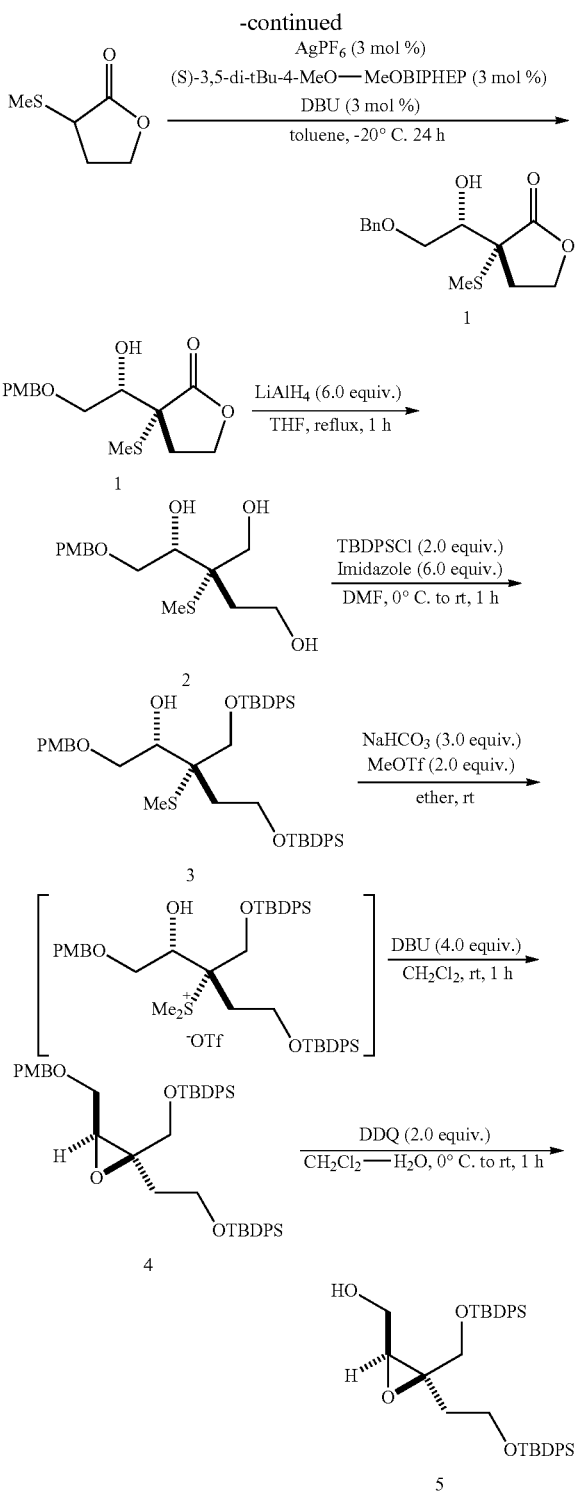

Here, symbols for the protective groups and substituents are as described above, and symbols for the compounds are described above and in the following Examples 1-1 to 1-5.

Example 1-1

<Synthesis of Compound 1>
α-Methylthio-γ-butyrolactone (320 μL, 3.00 mmol, synthesized by the technique of Barry M. Trost, Henry. C. Ardnt J. Org. Chem., 1973, 38, 3140-3144) and α-p-methoxybenzyloxyacetaldehyde (531 μL, 3.30 mmol, synthesized by the technique of Amos B. Smith, III and Richard J. Fox Org. Lett, 2004, 6, 1477-1480) were added in sequence to the catalyst solution 1 obtained in Production Example 1. After that, the solution was cooled to −20° C., and a 0.5M toluene solution (180 μL, 0.09 mmol) of 1,8-diazabicyclo[5.4.0]undec-7-ene (DBU) was added thereto, followed by stirring at the same temperature for 24 hours. After 24 hours, silica gel was added to the reaction solution in the same volume as the reaction solution, and then the mixture was allowed to pass through a silica gel short pad column, eluted with ethyl acetate, and concentrated under reduced pressure. Then, 1,1,2,2-tetrachloroethane (200 μL, 1.91 mmol) was added to the residue as an internal standard substance to obtain an NMR yield. The NMR yield was found to be 98% (sin/anti=12/1). The product was purified by flash column chromatography (hexane/ethyl acetate=4/1 (by volume)) and further purified by flash column chromatography (dichloromethane-dichloromethane/ethyl acetate=9/1 (by volume)) to thereby obtain the following compound 1 as a colorless oily substance. The yield amount was 800 mg (yield rate: 85%, optical purity: 98% ee).

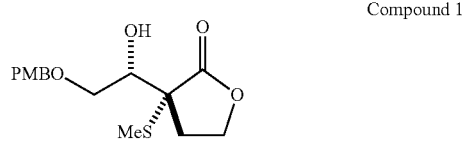

Compound 1

The following shows the results of $^1$H NMR spectrum (proton nuclear magnetic resonance spectrum), specific rotation, and HPLC (high-performance liquid chromatograph) of the obtained compound 1.

$^1$H NMR (CDCl$_3$): δ7.27-7.21 (m, 2H), 6.90-6.85 (m, 2H), 4.51 (d, J=11.7 Hz, 1H), 4.44 (d, J=11.7 Hz, 1H), 4.40 (ddd, J=6.4, 8.7, 10.3 Hz, 1H), 4.30 (ddd, J=1.6, 8.7, 9.0 Hz, 1H), 4.17 (ddd, J=2.1, 5.3, 6.2 Hz, 1H), 3.81 (s, 3H), 3.71 (dd, J=6.2, 9.8 Hz, 1H), 3.67 (dd, J=5.3, 9.8 Hz, 1H), 3.29 (d, J=2.1 Hz, 1H), 2.58 (ddd, J=9.0, 10.3, 14.0 Hz, 1H), 2.21 (s, 3H), 1.96 (ddd, J=1.6, 6.4, 14.0 Hz, 1H)

$[α]_D^{23}$ +27.9 (c 1.11, CHCl$_3$, 98% ee)

HPLC [Daicel CHIRALPAKAD-H, detection at 254 nm, 4:1 n-hexane/EtOH, flow rate=1.0 mL/min, t$_R$=20.6 min(minor), t$_R$=24.2 min(major)].

Example 1-2

<Synthesis of Compound 2>
In an argon atmosphere, anhydrous THF (15 mL) and lithium aluminum hydride (565 mg, 14.89 mmoL, 6.0 equivalents) were added to and stirred in a 100 mL recovery flask which had been dried under heating and vacuum. The resultant suspension was cooled on ice, and an anhydrous THF solution (10 mL) of the compound 1 (775 mg, 2.48 mmol, 1.0 equivalent) obtained in Example 1-1 was gradually added dropwise thereto. After generation of gas had settled, the mixture was refluxed under heating for 1 hour. The mixture was cooled to room temperature and then the obtained suspension was cooled on ice. Subsequently, 0.57 mL of water, 0.57 mL of a 15% by mass aqueous sodium hydroxide solution, and 1.71 mL of water were gradually added dropwise thereto in sequence. After that, the mixture was increased to room temperature, followed by stirring for a while. The obtained mixture was filtrated through a glass filter, eluted with ethyl acetate, and concentrated under reduced pressure.

The residue was purified by flash column chromatography (hexane/ethyl acetate=1/1 (by volume)-ethyl acetate) to thereby obtain the following compound 2 as a colorless oily substance. The yield amount was 641 mg (yield rate: 82%).

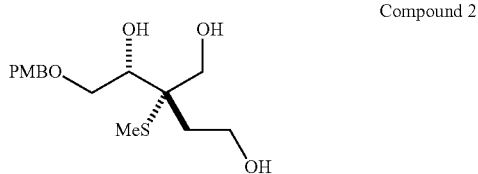

Compound 2

The following shows the results of $^1$H NMR spectrum (proton nuclear magnetic resonance spectrum) and specific rotation of the obtained compound 2.

$^1$H NMR (CDCl$_3$): δ7.28-7.24 (m, 2H), 6.91-6.86 (m, 2H), 4.53 (d, J=11.2 Hz, 1H), 4.49 (d, J=11.2 Hz, 1H), 3.94 (dd, J=4.4, 6.6 Hz, 1H), 3.90-3.82 (m, 2H), 3.81 (s, 3H), 3.78-3.62 (m, 4H), 3.36 (brs, 3H), 2.01 (s, 3H), 1.98-1.85 (m, 2H)

$[\alpha]_D^{23}$ −12.4 (c 0.98, CHCl$_3$).

Example 1-3

<Synthesis of Compound 3>

In a 20 mL recovery flask in an argon atmosphere, anhydrous DMF (3.9 mL) and imidazole (798 mg, 11.72 mmol, 6.0 equivalents) were added to the compound 2 (618 mg, 1.95 mmol, 1.0 equivalent) obtained in Example 1-2, followed by cooling to 0° C. in an ice bath. Next, tert-butyldiphenylchlorosilane (TBDPSCl, 1.0 mL, 3.91 mmol, 2.0 equivalents) was added thereto, and the mixture was stirred at room temperature for 1 hour. After that, an aqueous saturated ammonium chloride solution was added thereto to terminate the reaction. Water was added to the mixture, followed by extracting with diethyl ether three times. The combined organic layer was washed with saturated brine and dried with anhydrous sodium sulfate. After concentration under reduced pressure, the residue was purified by flash column chromatography (hexane-hexane/diethyl ether=4/1 (by volume)) to thereby obtain the following compound 3 as a yellow oily substance. The yield amount was 1.37 g (yield rate: 90%).

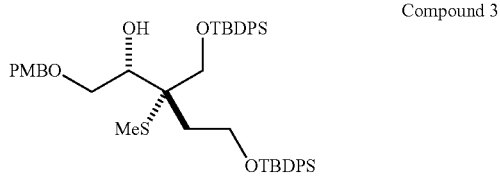

Compound 3

The following shows the results of 1H NMR spectrum (proton nuclear magnetic resonance spectrum) and specific rotation of the obtained compound 3.

$^1$H NMR (CDCl$_3$): δ7.70-7.63 (m, 8H), 7.48-7.34 (m, 12H), 7.27 (d, J=8.7 Hz, 2H), 6.88 (d, J=8.7 Hz, 2H), 4.51 (d, J=11.7 Hz, 1H), 4.47 (d, J=11.7 Hz, 1H), 4.08-4.04 (m, 1H), 3.99-3.90 (m, 1H), 3.87-3.75 (m, 6H), 3.72-3.61 (m, 2H), 3.17 (d, J=4.4 Hz, 1H), 2.09-1.99 (m, 1H), 1.96-1.87 (m, 1H), 1.85 (s, 3H), 1.08 (s, 9H), 1.06 (s, 9H)

$[\alpha]D^{23}$ −6.4 (c 4.20, CHCl$_3$)

Example 1-4

<Synthesis of Compound 4>

In an argon atmosphere, the compound 3 (79.3 mg, 0.10 mmol, 1.0 equivalent) obtained in Example 1-3, sodium hydrogen carbonate (25.2 mg, 0.30 mmol, 3.0 equivalents), and dry ether (1 mL) were added to a test tube which had been dried under heating and vacuum. Methyl triflate (MeOTf, 23 μL, 0.20 mmol, 2.0 equivalents) was gradually added dropwise thereto. The mixture was stirred until the starting materials were confirmed to disappear at room temperature and concentrated under reduced pressure. The residue was dissolved in anhydrous dichloromethane (1 mL) and 1,8-diazabicyclo[5.4.0]undec-7-ene (DBU) (60 μL, 0.40 mmol, 4.0 equivalents) was added dropwise to the solution, which was stirred for 1 hour at room temperature. Then, an aqueous saturated ammonium chloride solution was added thereto to terminate the reaction. The mixture was extracted with dichloromethane, and the combined organic layer was washed with saturated brine and dried with anhydrous sodium sulfate. After filtration and the subsequent concentration under reduced pressure, the residue was purified by flash column chromatography (hexane/diethyl ether=9/1 (by volume)) to thereby obtain the following compound 4 as a colorless oily substance. The yield amount was 45.2 mg (yield rate in two steps: 61%).

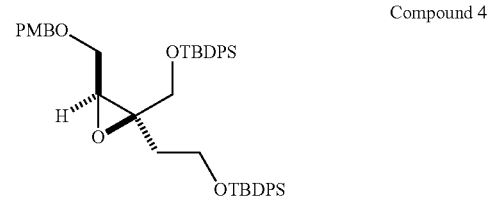

Compound 4

The following shows the results of 1H NMR spectrum (proton nuclear magnetic resonance spectrum) of the obtained compound 4.

$^1$H NMR (CDCl$_3$): δ7.68-7.60 (m, 8H), 7.45-7.32 (m, 12H), 7.20 (d, J=8.7 Hz, 1H), 6.83 (d, J=8.7 Hz, 1H), 4.47 (d, J=11.5 Hz, 1H), 4.35 (d, J=11.5 Hz, 1H), 3.83-3.78 (m, 5H), 3.74 (d, J=11.2 Hz, 1H), 3.67 (d, J=11.2 Hz, 1H), 3.61 (dd, J=2.8, 11.2 Hz, 1H), 3.31 (dd, J=6.9, 11.2 Hz, 1H), 3.23 (dd, J=2.8, 6.9 Hz, 1H), 2.35 (dt, J=5.7, 14.2 Hz, 1H), 1.81 (dt, J=7.1, 14.2 Hz, 1H), 1.04 (s, 9H), 1.03 (s, 9H)

Example 1-5

<Synthesis of Compound 5>

The compound 4 obtained in Example 1-4 (33 mg, 0.044 mmol, 1 equivalent) was dissolved in methylene chloride-water (methylene chloride/water=20/1 (by volume), 1 mL) in a test tube. Then, 2,3-dichloro-5,6-dicyano-p-benzoquinone (DDQ, 21 mg, 0.089 mmol) was added thereto at 0° C. and the mixture was increased to room temperature, followed by stirring for 1 hour. After that, the reaction mixture was filtrated through CELITE and washed with methylene chloride. The obtained solution was washed with saturated sodium bicarbonate water and saturated brine, and dried with anhydrous sodium sulfate. After filtration and the subsequent concentration under reduced pressure, the residue was purified by flash column chromatography (hexane/ethyl acetate=7/1 (by volume)) to thereby obtain the following compound 5 as a colorless oily substance. The yield amount was 22.4 mg (yield rate: 81%).

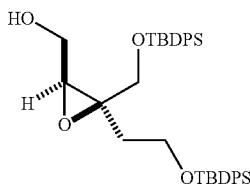

Compound 5

The following shows the results of 1H NMR spectrum (proton nuclear magnetic resonance spectrum) and specific rotation of the obtained compound 5.

$^1$H NMR (CDCl$_3$): δ7.66-7.60 (m, 8H), 7.45-7.32 (m, 12H), 3.79-3.54 (m, 6H), 3.18 (dd, J=5.0, 6.4 Hz, 1H), 2.23 (dt, J=6.0, 14.2 Hz, 1H), 1.82 (dt, J=6.9, 14.2 Hz, 1H), 1.71 (t, J=6.4 Hz, 1H), 1.04 (s, 9H), 1.03 (s, 9H)

$[\alpha]_D^{23}$ −3.0 (c 1.15, CHCl$_3$)

Example 2-1

<Synthesis of Compound 6>

In a glove box, AgPF$_6$ (15.2 mg, 0.06 mmol) and (S)-3,5-di-$^t$Bu-4-MeO-MeOBIPHEP (min. 97%) (71.2 mg, 0.06 mmol) were weighed in a 20 mL recovery flask which had been dried under heating and vacuum. The flask was taken out from the glove box, and anhydrous toluene (9.88 mL) was added thereto in an argon atmosphere, followed by stirring at room temperature for 30 min, thereby obtain catalyst solution.

α-Methylthio-γ-butyrolactone (213 μL, 2.00 mmol) and α-benzyloxyacetaldehyde (337 μL, 2.40 mmol) were added in sequence to the obtained catalyst solution. After that, the solution was cooled to −20° C., and a 0.5M toluene solution (120 μL, 0.06 mmol) of 1,8-diazabicyclo[5.4.0]undec-7-ene (DBU) was added thereto, followed by stirring at the same temperature for 48 hours. After 48 hours, silica gel was added to the reaction solution in the same volume as the reaction solution, and then the mixture was allowed to pass through a silica gel short pad column, eluted with hexane/ethyl acetate=1/1 (by volume), and concentrated under reduced pressure. The residue was purified by flash column chromatography (hexane/ethyl acetate=7/1-2/1 (by volume)) and further purified by flash column chromatography (dichloromethane-dichloromethane/ethyl acetate=9/1 (by volume)) to thereby obtain the following compound 6 as a colorless oily substance. The yield amount was 395 mg (yield rate: 70%, 98% ee).

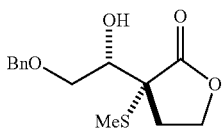

Compound 6

The following shows the results of 1H NMR spectrum (proton nuclear magnetic resonance spectrum) and HPLC (high-performance liquid chromatograph) of the obtained compound 6.

$^1$H NMR (CDCl$_3$): δ7.38-7.27 (m, 5H), 4.58 (d, J=11.9 Hz, 1H), 4.52 (d, J=11.9 Hz, 1H), 4.40 (ddd, J=6.4, 8.9, 10.3 Hz, 1H), 4.30 (ddd, J=1.8, 8.7, 8.9 Hz, 1H), 4.19 (m, 1H), 3.73 (m, 2H), 3.33 (d, J=1.8 Hz, 1H), 2.60 (ddd, J=8.7, 10.3, 14.0 Hz, 1H), 2.21 (s, 3H), 1.98 (ddd, J=1.8, 6.4, 14.0 Hz, 1H).

HPLC [Daicel CHIRALPAKAD-H, detection at 254 nm, 9:1 n-hexane/EtOH, flow rate=1.0 mL/min, t$_R$=26.2 min(minor), t$_R$=33.0 min(major)].

Example 2-2

<Synthesis of Compound 7>

In an argon atmosphere, anhydrous THF (8 mL) and lithium aluminum hydride (315 mg, 8.29 mmol, 6.0 equivalents) were added to and stirred in a 50 mL recovery flask which had been dried under heating and vacuum. An anhydrous THF solution (5.8 mL) of the compound 6 obtained in Example 2-1 (390 mg, 1.38 mmol, 1 equivalent) was gradually added dropwise to the resultant suspension in ice bath. After generation of gas had settled, the mixture was refluxed under heating for 1 hour. The mixture was left to gradually cool to room temperature. Subsequently, 0.32 mL of water, 0.32 mL of a 15% by mass aqueous sodium hydroxide solution, and 0.96 mL of water were gradually added dropwise thereto in sequence. After that, the mixture was increased to room temperature, followed by stirring for a while. The obtained mixture was filtrated through CELITE, eluted with ethyl acetate, and concentrated under reduced pressure. The residue was purified by flash column chromatography (hexane/ethyl acetate=1/3 (by volume)) to thereby obtain the following compound 7 as a colorless oily substance. The yield amount was 351 mg (yield rate: 89%).

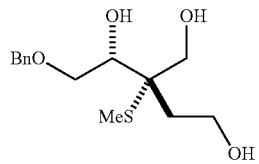

Compound 7

The following shows the results of $^1$H NMR spectrum (proton nuclear magnetic resonance spectrum) of the obtained compound 7.

$^1$H NMR (CDCl$_3$): δ7.38-7.27 (m, 5H), 4.60 (d, J=11.7 Hz, 1H), 4.56 (d, J=11.7 Hz, 1H), 3.97 (m, 1H), 3.88-3.64 (m, 6H), 3.12 (brs, 3H), 2.01 (s, 3H), 1.98-1.82 (m, 2H).

Example 2-3

<Synthesis of Compound 8>

In an argon atmosphere, in a 20 mL recovery flask which had been dried under heating and vacuum, DMF (2.4 mL) and imidazole (481 mg, 7.06 mmol, 6 equivalents) were added to the compound 7 (337 mg, 1.18 mmol, 1 equivalent) obtained in Example 2-2, followed by cooling to 0° C. in an ice bath. tert-Butyldiphenylchlorosilane (0.61 mL, 2.35 mmol, 2.0 equivalents) was added thereto, and the mixture was stirred at room temperature for 1 hour. After that, an aqueous saturated ammonium chloride solution was added thereto to terminate the reaction. The mixture was extracted with diethyl ether, and the combined organic layer was washed with saturated brine and dried with anhydrous sodium sulfate. After concentration under reduced pressure, the residue was purified by flash column chromatography (hexane/ether acetate=9/1 (by volume)) to thereby obtain the following compound 8 as a colorless oily substance. The yield amount was 884 mg (yield rate: 98%).

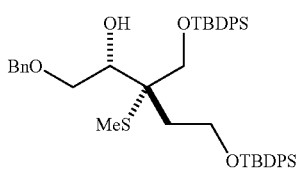

Compound 8

The following shows the results of 1H NMR spectrum (proton nuclear magnetic resonance spectrum) of the obtained compound 8.

$^1$H NMR (CDCl$_3$): δ7.68-7.61 (m, 8H), 7.46-7.26 (m, 17H), 4.57 (d, J=11.9 Hz, 1H), 4.53 (d. J=11.9 Hz, 1H), 4.08-4.03 (m, 1H), 3.96-3.89 (m, 1H), 3.85-3.75 (m, 3H), 3.71-3.61 (m, 2H), 3.17 (d, J=4.6 Hz, 1H), 2.08-1.97 (m, 1H), 1.93-1.84 (m, 1H), 1.83 (s, 3H), 1.06 (s, 9H), 1.04 (s, 9H).

Example 2-4

<Synthesis of Compound 9>

In a test tube in an argon atmosphere, dry ether (2.6 mL) was added to the compound 8 obtained in Example 2-3 (200 mg, 0.26 mmol, 1.0 equivalent), followed by cooling to 0° C. in an ice bath. Methyl triflate (44 μL, 0.39 mmol, 1.5 equivalents) was gradually added dropwise thereto. The mixture was stirred until the starting materials were confirmed to disappear at room temperature and concentrated under reduced pressure. The residue was dissolved in anhydrous dichloromethane (2.6 mL) and 1,8-diazabicyclo[5.4.0]undec-7-ene (DBU) (0.12 mL, 0.79 mmol, 3 equivalents) was added dropwise to the solution, which was stirred for 2 hours at room temperature. Then, an aqueous saturated ammonium chloride solution was added thereto to terminate the reaction. The mixture was extracted with dichloromethane, and the combined organic layer was washed with saturated brine and dried with anhydrous sodium sulfate. The residue was purified by flash column chromatography (hexane/diethyl ether=9/1 (by volume)) to thereby obtain the following compound 9 as a colorless oily substance. The yield amount was 99.8 mg (yield rate in two steps: 54%).

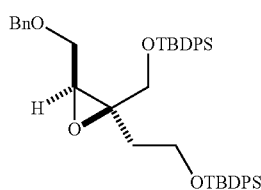

Compound 9

The following shows the results of $^1$H NMR spectrum (proton nuclear magnetic resonance spectrum) of the obtained compound 9.

$^1$H NMR (CDCl$_3$): δ7.66-7.58 (m, 8H), 7.43-7.26 (m, 17H), 4.52 (d, J=11.9 Hz, 1H), 4.39 (d, J=11.9 Hz, 1H), 3.79 (dd, J=5.7, 6.9 Hz, 2H), 3.72 (d, J=11.4 Hz, 1H), 3.65 (d, J=11.4 Hz, 1H), 3.62 (dd, J=3.0, 11.2 Hz, 1H), 3.31 (dd, J=6.9, 11.2 Hz, 1H), 3.23 (dd, J=3.0, 6.9 Hz, 1H), 2.33 (dt, J-=5.7, 14.2 Hz, 1H), 1.79 (dt, J=6.9, 14.2 Hz, 1H), 1.02 (s, 9H), 1.01 (s, 9H).

Example 2-5

<Synthesis of Compound 5>

The compound 9 obtained in Example 2-4 (147 mg, 0.21 mmol, 1 equivalent), ethyl acetate (4 mL), and palladium/carbon (29.4 mg, 20% mass/mass) were added to a test tube. The mixture was stirred for 21 hours at room temperature in a hydrogen atmosphere of 1 atm. After that, unnecessary substances were filtered off through CELITE and the filtrate was concentrated under reduced pressure. The residue was purified by flash column chromatography (hexane/ethyl acetate=7/1 (by volume)) to thereby obtain the following compound 5 as a colorless oily substance. The yield amount was 45 mg (yield rate: 35%).

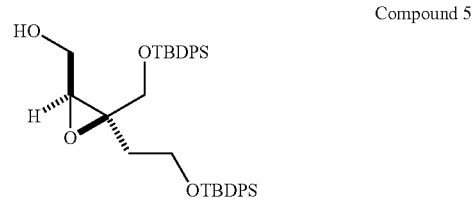

Compound 5

The following shows the results of $^1$H NMR spectrum (proton nuclear magnetic resonance spectrum) of the obtained compound 5.

$^1$H NMR (CDCl$_3$): δ7.66-7.60 (m, 8H), 7.45-7.32 (m, 12H), 3.79-3.54 (m, 6H), 3.18 (dd, J=5.0, 6.4 Hz, 1H), 2.24 (dt, J=6.0, 14.2 Hz, 1H), 1.82 (dt, J=6.9, 14.2 Hz, 1H), 1.77 (brs, 1H), 1.04 (s, 9H), 1.03 (s, 9H).

Example 3

<Synthesis of Compound 1 (Synthesis Example in which the Silver Compound in a Catalyst was Changed)>

α-Methylthio-γ-butyrolactone (21 μL, 0.20 mmol, 1.0 equivalent) and α-p-methoxybenzyloxyacetaldehyde (39 μL, 0.24 mmol, 1.2 equivalents) were added in sequence to the catalyst solution 2 obtained in Production Example 2. After that, the solution was cooled to −20° C., and a 0.5M toluene solution (20 μL, 0.01 mmol, 0.05 equivalents) of 1,8-diazabicyclo[5.4.0]undec-7-ene (DBU) was added thereto, followed by stirring at the same temperature (−20° C.) for 24 hours. After 24 hours, silica gel was added to the reaction solution in the same volume as the reaction solution, and then the mixture was allowed to pass through a silica gel short pad column, eluted with ethyl acetate, and concentrated under reduced pressure, to thereby obtain compound 1. Then, 1,1,2,2-tetrachloroethane (20 μL, 0.19 mmol) was added to the residue as an internal standard substance to obtain an NMR yield. Optical purity (ee) was determined by HPLC. The NMR yield was found to be 85% (sin/anti=18/1) and the optical purity was found to be 98% ee.

Example 4

<Synthesis of Compound 1 (Synthesis Example in which the Silver Compound in a Catalyst was Changed)>

α-Methylthio-γ-butyrolactone (21 μL, 0.20 mmol, 1.0 equivalent) and α-p-methoxybenzyloxyacetaldehyde (39 μL, 0.24 mmol, 1.2 equivalents) were added in sequence to the catalyst solution 3 obtained in Production Example 3. After that, the solution was cooled to −20° C., and a 0.5M toluene solution (20 μL, 0.01 mmol, 0.05 equivalents) of 1,8-diazabicyclo[5.4.0]undec-7-ene (DBU) was added thereto, followed by stirring at the same temperature (−20° C.) for 24 hours. After 24 hours, silica gel was added to the reaction solution in the same volume as the reaction solution, and then the mixture was allowed to pass through a silica gel short pad column, eluted with ethyl acetate, and concentrated under reduced pressure, to thereby obtain compound 1. Then, 1,1,2,2-tetrachloroethane (20 μL, 0.19 mmol) was added to the residue as an internal standard substance to obtain an NMR yield. Optical purity (ee) was determined by HPLC. The NMR yield was found to be 93% (sin/anti=8/1) and the optical purity was found to be 97% ee.

Example 5

<Synthesis of Compound 1 (Synthesis Example in which the Silver Compound in a Catalyst was Changed)>
α-Methylthio-γ-butyrolactone (21 μL, 0.20 mmol, 1.0 equivalent) and α-p-methoxybenzyloxyacetaldehyde (39 μL, 0.24 mmol, 1.2 equivalents) were added in sequence to the catalyst solution 4 obtained in Production Example 4. After that, the solution was cooled to −20° C., and a 0.5M toluene solution (20 μL, 0.01 mmol, 0.05 equivalents) of 1,8-diazabicyclo[5.4.0]undec-7-ene (DBU) was added thereto, followed by stirring at the same temperature (−20° C.) for 24 hours. After 24 hours, silica gel was added to the reaction solution in the same volume as the reaction solution, and then the mixture was allowed to pass through a silica gel short pad column, eluted with ethyl acetate, and concentrated under reduced pressure, to thereby obtain compound 1. Then, 1,1,2,2-tetrachloroethane (20 μL, 0.19 mmol) was added to the residue as an internal standard substance to obtain an NMR yield. Optical purity (ee) was determined by HPLC. The NMR yield was found to be >99% (sin/anti=10/1) and the optical purity was found to be 97% ee.

Example 6

<Synthesis of Compound 10>
Anhydrous toluene (0.78 mL), α-methylthio-γ-butyrolactone (21 μL, 0.20 mmol, 1.0 equivalent), (tert-butyldimethylsilyloxy)acetaldehyde (47 μL, 0.24 mmol, 1.2 equivalents), and the catalyst solution 5 obtained in Production Example 5 (200 μL, 0.01 mmol, 0.05 equivalents) were added in sequence to a brown test tube which had been dried under heating and vacuum. After that, the solution was cooled to −20° C., and a 0.5M toluene solution (20 μL, 0.01 mmol, 0.05 equivalents) of 1,8-diazabicyclo[5.4.0]undec-7-ene (DBU) was added thereto, followed by stirring at the same temperature (−20° C.) for 48 hours. Silica gel was added to the reaction solution in the same volume as the reaction solution, and then the mixture was allowed to pass through a silica gel short pad column, eluted with ethyl acetate, and concentrated under reduced pressure. The residue was purified by flash column chromatography (hexane/ethyl acetate=19/1 (by volume)) to thereby obtain the following compound 10 (yield amount: 54.4 mg, sin/anti=>20/1, yield rate: 89%, 98% ee).

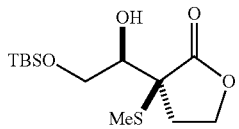

Compound 10

The following shows the results of $^1$H NMR spectrum (proton nuclear magnetic resonance spectrum) of the obtained compound 10.
$^1$H NMR (CDCl$_3$): δ4.41 (ddd, J=6.4, 8.7, 10.1 Hz, 1H), 4.34 (ddd, J=1.8, 8.7, 8.9 Hz, 1H), 4.03 (ddd, J=2.1, 5.7, 6.2 Hz, 1H), 3.86 (dd, J=5.7, 10.3 Hz, 1H), 3.83 (dd, J=6.2, 10.3 Hz, 1H), 3.32 (d, J=2.1 Hz, 1H), 2.68 (ddd, J=8.9, 10.1, 14.0 Hz, 1H), 2.21 (s, 3H), 2.00 (ddd, J=1.8, 6.4, 14.0 Hz, 1H), 0.89 (s, 9H), 0.08 (s, 3H), 0.08 (s, 3H)

Example 7

<Synthesis of Compound 11>
Anhydrous toluene (0.87 mL), α-methylthio-γ-butyrolactone (21 μL, 0.20 mmol, 1.0 equivalent), hydrocinnamaldehyde (32 μL, 0.24 mmol, 1.2 equivalents), and the catalyst solution 5 obtained in Production Example 5 (120 μL, 0.006 mmol, 0.03 equivalents) were added in sequence to a brown test tube which had been dried under heating and vacuum. After that, the solution was cooled to −20° C., and a 0.5M toluene solution (12 μL, 0.006 mmol, 0.03 equivalents) of 1,8-diazabicyclo[5.4.0]undec-7-ene (DBU) was added thereto, followed by stirring at the same temperature (−20° C.) for 48 hours. Silica gel was added to the reaction solution in the same volume as the reaction solution, and then the mixture was allowed to pass through a silica gel short pad column, eluted with ethyl acetate, and concentrated under reduced pressure. The residue was purified by flash column chromatography (hexane/ethyl acetate=9/1 (by volume)) to thereby obtain the following compound 11 (yield amount: 49.8 mg, sin/anti=18/1, yield rate: 93%, 98% ee).

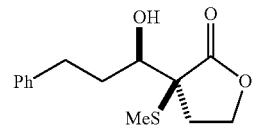

Compound 11

The following shows the results of 1H NMR spectrum (proton nuclear magnetic resonance spectrum) of the obtained compound 11.
$^1$H NMR (CDCl$_3$): δ7.32-7.27 (m, 2H), 7.24-7.17 (m, 3H), 4.41 (ddd, J=6.4, 8.9, 10.8 Hz, 1H), 4.30 (ddd, J=1.2, 8.9, 9.0 Hz, 1H), 3.92 (m, 1H), 3.23 (m, 1H), 3.00 (ddd, J=4.8, 10.3, 13.8 Hz, 1H), 2.73 (ddd, J=6.9, 9.8, 13.8 Hz, 1H), 2.41 (ddd, J=9.0, 10.8, 14.0 Hz, 1H), 2.22 (s, 3H), 2.04-1.94 (m, 1H), 1.90 (ddd, J=1.2, 6.4, 14.0 Hz, 1H), 1.66-1.58 (m, 1H)

Example 8

<Synthesis of Compound 12>
Anhydrous toluene (0.78 mL), α-methylthio-γ-butyrolactone (21 μL, 0.20 mmol, 1.0 equivalent), octanal (38 μL, 0.24 mmol, 1.2 equivalents), and the catalyst solution 5 obtained in Production Example 5 (200 μL, 0.01 mmol, 0.05 equivalents) were added in sequence to a brown test tube which had been dried under heating and vacuum. After that, the solution was cooled to −20° C., and a 0.5M toluene solution (20 μL, 0.01 mmol, 0.05 equivalents) of 1,8-diazabicyclo[5.4.0]undec-7-ene (DBU) was added thereto, followed by stirring at the same temperature (−20° C.) for 48 hours. After 48 hours, silica gel was added to the reaction solution in the same volume as the reaction solution, and then the mixture was allowed to pass through a silica gel short pad column, eluted with ethyl acetate, and concentrated under reduced pressure.

The residue was purified by flash column chromatography (hexane/ethyl acetate=19/1 (by volume)) to thereby obtain the following compound 12 (yield amount: 40.0 mg, sin/anti=13/1, yield rate: 77%, 99% ee).

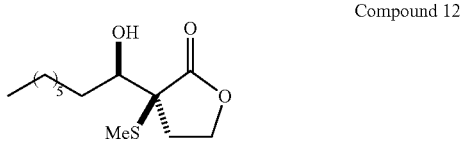

Compound 12

The following shows the results of $^1$H NMR spectrum (proton nuclear magnetic resonance spectrum) of the obtained compound 12.

$^1$H NMR (CDCl$_3$): δ4.40 (ddd, J=6.2, 8.9, 10.6 Hz, 1H), 4.33 (ddd, J=1.4, 8.9, 9.0 Hz, 1H), 3.87 (m, 1H), 3.09 (s, 1H), 2.49 (ddd, J=9.0, 10.6, 14.0 Hz, 1H), 2.20 (s, 3H), 1.89 (ddd, J=1.4, 6.2, 14.0 Hz, 1H), 1.68-1.56 (m, 2H), 1.45-1.21 (m, 10H), 0.87 (t, J=7.1 Hz, 3H)

Example 9

<Synthesis of Compound 13>

Anhydrous toluene (0.78 mL), α-methylthio-δ-valerolactone (25 μL, 0.20 mmol, 1.0 equivalent), α-benzyloxyacetaldehyde (34 μL, 0.24 mmol, 1.2 equivalents), and the catalyst solution 5 obtained in Production Example 5 (200 μL, 0.01 mmol, 0.05 equivalents) were added in sequence to a brown test tube which had been dried under heating and vacuum. After that, the solution was cooled to −20° C., and a 0.5M toluene solution (20 μL, 0.01 mmol, 0.05 equivalents) of 1,8-diazabicyclo[5.4.0]undec-7-ene (DBU) was added thereto, followed by stirring at the same temperature (−20° C.) for 32 hours. After 32 hours, silica gel was added to the reaction solution in the same volume as the reaction solution, and then the mixture was allowed to pass through a silica gel short pad column, eluted with ethyl acetate, and concentrated under reduced pressure. The residue was purified by flash column chromatography (hexane/ethyl acetate=3/1 (by volume)) to thereby obtain the following compound 13 (yield amount: 36.3 mg, sin/anti=16/1, yield rate: 61%, 99% ee).

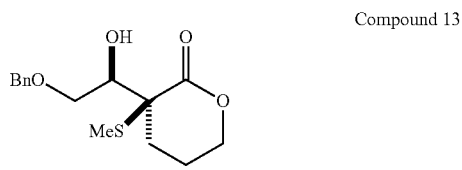 [SMILES: CS[C@]1([C@H](O)COCc2ccccc2)CCCOC1=O]

Compound 13

The following shows the results of $^1$H NMR spectrum (proton nuclear magnetic resonance spectrum) of the obtained compound 13.

$^1$H NMR (CDCl$_3$): δ7.37-7.27 (m, 5H), 4.58 (d, J=11.9 Hz, 1H), 4.52 (d, J=11.9 Hz, 1H), 4.50-4.44 (m, 1H), 4.36-4.32 (m, 1H), 4.24-4.18 (m, 1H), 3.71 (dd, J=6.4, 9.8 Hz, 1H), 3.65 (dd, J=4.6, 9.8 Hz, 1H), 2.94 (m, 1H), 2.31-2.18 (m, 1H), 2.17-2.04 (m, 4H), 1.78-1.68 (m, 2H)

Example 10

<Synthesis of Compound 14>

Anhydrous toluene (0.78 mL), α-methylthio-γ-butyrolactone (21 μL, 0.20 mmol, 1.0 equivalent), α-p-methoxybenzyloxyacetaldehyde (39 μL, 0.24 mmol, 1.2 equivalents), and the catalyst solution 5 obtained in Production Example 5 (0.05M toluene solution, 200 μL, 0.01 mmol, 0.05 equivalents) were added in sequence to a brown test tube which had been dried under heating and vacuum. After that, the solution was cooled to −20° C., and a 0.5M toluene solution (20 μL, 0.01 mmol, 0.05 equivalents) of triethylamine was added thereto, followed by stirring at the same temperature for 24 hours. Silica gel was added to the reaction solution in the same volume as the reaction solution, and then the mixture was allowed to pass through a silica gel short pad column, eluted with ethyl acetate, and concentrated under reduced pressure, to thereby obtain the following compound 14. Then, 1,1,2,2-tetrachloroethane (20 μL, 0.19 mmol) was added to the residue as an internal standard substance to obtain an NMR yield. Optical purity (ee) was determined by HPLC. The NMR yield was found to be 4% (sin/anti=10/1) and the optical purity was found to be 39% ee.

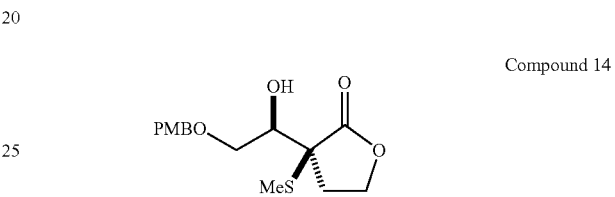

Compound 14

The following shows the results of $^1$H NMR spectrum (proton nuclear magnetic resonance spectrum) and HPLC (high-performance liquid chromatograph) of the compound 14 obtained in Example 10.

$^1$H NMR (CDCl$_3$): δ7.27-7.21 (m, 2H), 6.90-6.85 (m, 2H), 4.51 (d, J=11.7 Hz, 1H), 4.44 (d, J=11.7 Hz, 1H), 4.40 (ddd, J=6.4, 8.7, 10.3 Hz, 1H), 4.30 (ddd, J=1.6, 8.7, 9.0 Hz, 1H), 4.17 (ddd, J=2.1, 5.3, 6.2 Hz, 1H), 3.81 (s, 3H), 3.71 (dd, J=6.2, 9.8 Hz, 1H), 3.67 (dd, J=5.3, 9.8 Hz, 1H), 3.29 (d, J=2.1 Hz, 1H), 2.58 (ddd, J=9.0, 10.3, 14.0 Hz, 1H), 2.21 (s, 3H), 1.96 (ddd, J=1.6, 6.4, 14.0 Hz, 1H)

HPLC [Daicel CHIRALPAK AD-H, detection at 254 nm, 4:1 n-hexane/EtOH, flow rate=1.0 mL/min, t$_R$=21.3 min(major), t$_R$=25.0 min(minor)].

Example 11

<Synthesis of Compound 14 (Synthesis Example in which the Base was Changed)>

Anhydrous toluene (0.80 mL), α-methylthio-γ-butyrolactone (21 μL, 0.20 mmol, 1.0 equivalent), α-p-methoxybenzyloxyacetaldehyde (39 μL, 0.24 mmol, 1.2 equivalents), and the catalyst solution 5 obtained in Production Example 5 (0.05M toluene solution, 200 μL, 0.01 mmol, 0.05 equivalents) were added in sequence to a brown test tube which had been dried under heating and vacuum. After that, the solution was cooled to −20° C., and 1,5,7-triazacyclo[4.4.0]dec-5-ene (1.4 mg, 0.01 mmol, 0.05 equivalents) was added thereto, followed by stirring at the same temperature for 24 hours. Silica gel was added to the reaction solution in the same volume as the reaction solution, and then the mixture was allowed to pass through a silica gel short pad column, eluted with ethyl acetate, and concentrated under reduced pressure, to thereby obtain the following compound 14. Then, 1,1,2,2-tetrachloroethane (20 μL, 0.19 mmol) was added to the residue as an internal standard substance to obtain an NMR yield. Optical purity (ee) was determined by HPLC. The NMR yield was found to be 99% (sin/anti=6/1) and the optical purity was found to be 95% ee.

The following shows the results of ¹H NMR spectrum (proton nuclear magnetic resonance spectrum) and HPLC (high-performance liquid chromatograph) of the compound 14 obtained in Example 11.

¹H NMR (CDCl$_3$): δ7.27-7.21 (m, 2H), 6.90-6.85 (m, 2H), 4.51 (d, J=11.7 Hz, 1H), 4.44 (d, J=11.7 Hz, 1H), 4.40 (ddd, J=6.4, 8.7, 10.3 Hz, 1H), 4.30 (ddd, J=1.6, 8.7, 9.0 Hz, 1H), 4.17 (ddd, J=2.1, 5.3, 6.2 Hz, 1H), 3.81 (s, 3H), 3.71 (dd, J-=6.2, 9.8 Hz, 1H), 3.67 (dd, J=5.3, 9.8 Hz, 1H), 3.29 (d, J=2.1 Hz, 1H), 2.58 (ddd, J=9.0, 10.3, 14.0 Hz, 1H), 2.21 (s, 3H), 1.96 (ddd, J=1.6, 6.4, 14.0 Hz, 1H)

HPLC [Daicel CHIRALPAK AD-H, detection at 254 nm, 4:1 n-hexane/EtOH, flow rate=1.0 mL/min, t$_R$=21.1 min(major), t$_R$=25.4 min(minor)].

Embodiments of the present invention are as follows, for example.

<1> A compound represented by the following General Formula (1):

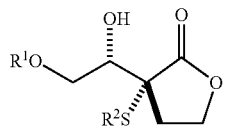

General Formula (1)

where R¹ represents a protective group for a hydroxyl group or a hydrogen atom, and R² represents a methyl group or an ethyl group.

<2> A compound represented by the following General Formula (2):

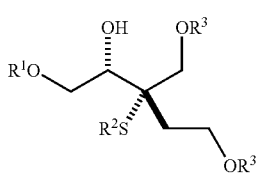

General Formula (2)

where R¹ represents a protective group for a hydroxyl group or a hydrogen atom, R² represents a methyl group or an ethyl group, and R³ represents a protective group for a hydroxyl group or a hydrogen atom.

<3> A compound represented by the following General Formula (3):

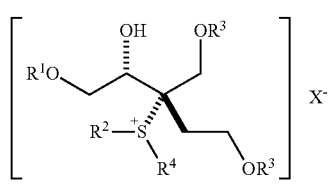

General Formula (3)

where R¹ represents a protective group for a hydroxyl group or a hydrogen atom, R² represents a methyl group or an ethyl group, R³ represents a protective group for a hydroxyl group or a hydrogen atom, R⁴ represents a methyl group or an ethyl group, and X⁻ represents a monovalent anion.

<4> An asymmetric synthesis reaction, including:
allowing a compound represented by the following General Formula (4) and a compound represented by the following General Formula (5) to react with each other in the presence of a chiral silver complex obtained from a silver compound and a compound represented by the following General Formula (A) to thereby obtain a compound represented by the following General Formula (6):

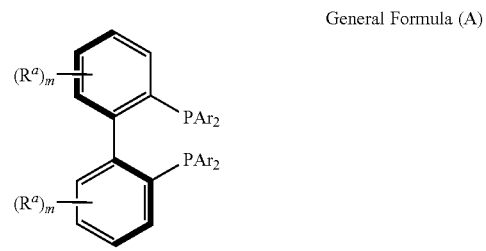

General Formula (A)

where R$^a$ each independently represents a hydrogen atom, an alkyl group, an alkoxy group, an alkenyl group, an aryl group, an arylalkyl group, an arylalkenyl group, a non-aromatic heterocyclic ring, or an aromatic heterocyclic ring, m is an integer of 1 or 2; when m is 2, two R$^a$ may be bonded together to form a ring structure; and Ar represents an aryl group which may have a substituent,

General Formula (4)

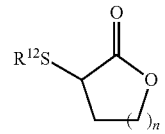

General Formula (5)

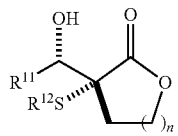

General Formula (6)

where in General Formulas (4) to (6), R¹¹ represents a hydrogen atom or a substituent, R¹² represents a methyl group or an ethyl group, and n is an integer of 1 to 3.

<5> The asymmetric synthesis reaction according to <4>, wherein the silver compound is AgPF$_6$, AgBF$_4$, or AgSbF$_6$, and the compound represented by General Formula (A) is a compound represented by the following General Formula (A-1):

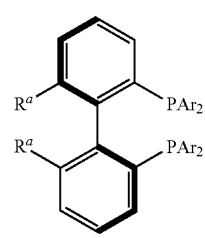

General Formula (A-1)

where R$^a$ represents a methoxy group, and Ar represents a 3,5-di-tert-butyl-4-methoxyphenyl group.

<6> An asymmetric synthesis reaction, including:
allowing a compound represented by the following General Formula (4) and a compound represented by the following General Formula (5) to react with each other in the presence of a chiral silver complex obtained from a silver compound and a compound represented by the following General Formula (B) to thereby obtain a compound represented by the following General Formula (7):

General Formula (B)

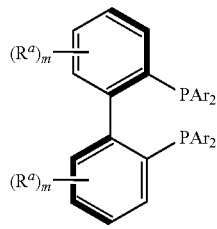

where $R^a$ each independently represents a hydrogen atom, an alkyl group, an alkoxy group, an alkenyl group, an aryl group, an arylalkyl group, an arylalkenyl group, a non-aromatic heterocyclic ring, or an aromatic heterocyclic ring, m is an integer of 1 or 2; when m is 2, two $R^a$ may be bonded together to form a ring structure; and Ar represents an aryl group which may have a substituent, General Formula (4)

General Formula (5)

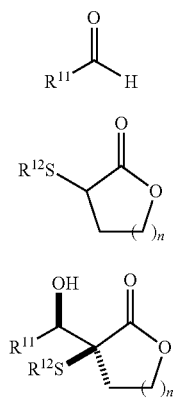

General Formula (7)

where in General Formulas (4) and (7), $R^{11}$ represents a hydrogen atom or a substituent, and in General Formulas (5) and (7), $R^{12}$ represents a methyl group or an ethyl group, and n is an integer of 1 to 3.

<7> The asymmetric synthesis reaction according to <6>, wherein the silver compound is $AgPF_6$, $AgBF_4$, or $AgSbF_6$, and the compound represented by General Formula (B) is a compound represented by the following General Formula (B-1):

General Formula (B-1)

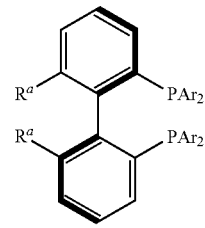

where $R^a$ represents a methoxy group, and Ar denotes a 3,5-di-tert-butyl-4-methoxyphenyl group.

Industrial Applicability

The compound of the present invention represented by General Formula (1), the compound of the present invention represented by General Formula (2), and the compound of the present invention represented by General Formula (3) enable compounds useful for production of pharmaceutical drugs such as anti-hepatitis C virus drugs to be synthesized at low cost by a technique of synthetic organic chemistry, and thus are useful as intermediates in syntheses of compounds used for pharmaceutical drugs such as anti-hepatitis C virus drugs.

The asymmetric synthesis reaction of the present invention enables compounds useful for production of pharmaceutical drugs such as anti-hepatitis C virus drugs to be synthesized at low cost by a technique of synthetic organic chemistry, and thus is useful for production of pharmaceutical drugs such as anti-hepatitis C virus drugs.

What is claimed is:

1. A compound represented by the following General Formula (3):

General Formula (3)

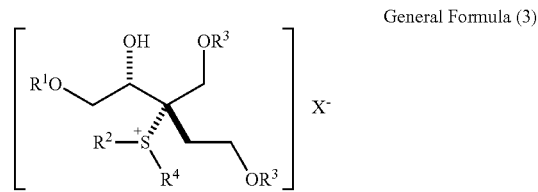

where $R^4$ represents a protective group for a hydroxyl group or a hydrogen atom, $R^2$ represents a methyl group or an ethyl group, $R^3$ represents a protective group for a hydroxyl group or a hydrogen atom, $R^4$ represents a methyl group or an ethyl group, and $X^-$ represents a monovalent anion.

* * * * *